(12) United States Patent
Hunsberger

(10) Patent No.: US 11,623,098 B2
(45) Date of Patent: Apr. 11, 2023

(54) BIPOLAR AND TRIPOLAR CONFIRGURATION FOR UNIDIRECTIONAL STIMULATION OF A-TYPE NERVE FIBERS

(71) Applicant: Galvani Bioelectronics Limited, Brentford (GB)

(72) Inventor: Gerald Edwin Hunsberger, Brentford (GB)

(73) Assignee: Galvani Bioelectronics Limited, Brentford (GB)

( * ) Notice: Subject to any disclaimer, the term of this patent is extended or adjusted under 35 U.S.C. 154(b) by 0 days.

(21) Appl. No.: 15/733,223

(22) PCT Filed: Dec. 11, 2018

(86) PCT No.: PCT/GB2018/053597
§ 371 (c)(1),
(2) Date: Jun. 11, 2020

(87) PCT Pub. No.: WO2019/116027
PCT Pub. Date: Jun. 20, 2019

(65) Prior Publication Data
US 2021/0093868 A1 Apr. 1, 2021

Related U.S. Application Data

(60) Provisional application No. 62/609,184, filed on Dec. 21, 2017, provisional application No. 62/597,227, filed on Dec. 11, 2017.

(51) Int. Cl.
*A61N 1/36* (2006.01)
*A61N 1/05* (2006.01)

(52) U.S. Cl.
CPC ....... *A61N 1/36178* (2013.01); *A61N 1/0556* (2013.01); *A61N 1/36175* (2013.01); *A61N 1/36182* (2013.01)

(58) Field of Classification Search
CPC .............. A61N 1/36178; A61N 1/0556; A61N 1/36175; A61N 1/36182; A61N 1/20; A61N 1/36185; A61N 1/36064; A61N 1/205
See application file for complete search history.

(56) References Cited

U.S. PATENT DOCUMENTS 4,628,942 A * 12/1986 Sweeney .............. A61N 1/0556
607/118
5,324,322 A * 6/1994 Grill, Jr ................... A61N 1/05
600/375

(Continued)

OTHER PUBLICATIONS

International Search Report and Written Opinion, International Application No. PCT/GB2018/053597, dated Jul. 17, 2019, 12 pages.

(Continued)

*Primary Examiner* — Mallika D Fairchild
(74) *Attorney, Agent, or Firm* — Merchant & Gould P.C.

(57) ABSTRACT

There is provided a neural interface device for unidirectional stimulation of a nerve including at least one A-type nerve fiber or at least one at least partially myelinated nerve fiber. The device includes an electrode arrangement for placing on or around the nerve. The electrode arrangement includes a first electrode configured to be positively charged and a second electrode configured to be negatively charged, where the surface area of the second electrode is larger than the surface area of first electrode.

22 Claims, 16 Drawing Sheets

(56) References Cited

U.S. PATENT DOCUMENTS

| | | | |
|---|---|---|---|
| 2003/0045909 A1* | 3/2003 | Gross | A61N 1/36114 607/9 |
| 2006/0136024 A1 | 6/2006 | Cohen et al. | |
| 2008/0147137 A1* | 6/2008 | Cohen | A61N 1/3616 607/17 |
| 2012/0130463 A1* | 5/2012 | Ben-David | A61N 1/0556 607/118 |
| 2014/0214135 A1* | 7/2014 | Ben-David | A61N 1/0556 607/116 |
| 2014/0228905 A1 | 8/2014 | Bolea | |
| 2015/0202433 A1* | 7/2015 | Franke | A61N 1/0551 607/118 |
| 2016/0199651 A1* | 7/2016 | Meadows | A61N 1/36185 607/42 |
| 2018/0161570 A1* | 6/2018 | Renaux | A61N 1/0558 |
| 2020/0316372 A1 | 10/2020 | Bashirullah et al. | |
| 2020/0384265 A1 | 12/2020 | Donega et al. | |
| 2021/0093867 A1 | 4/2021 | Donega et al. | |
| 2021/0138238 A1 | 5/2021 | Holder et al. | |

OTHER PUBLICATIONS

Sweeney, James D. et al., "An Asymmetric Two Electrode Cuff for Generation of Unidirectional Propagated Action Potentials", IEEE Transactions on Biomedical Engineering, vol. 33, pp. 541-549, Jun. 1986.

Van Den Honert, Christopher et al., "Generation of Unidirectionally Propagated Action Potentials in a Peripheral Nerve by Brief Stimuli", Science, vol. 206, No. 4424, Dec. 14, 1979 pp. 1311-1312.

Van Den Honert, Christopher et al., "A Technique for Collision Block of Peripheral Nerve: Single Stimulus Analysis", IEEE Transactions on Biomedical Engineering, vol. BMF-28, No. 5, May 1981.

* cited by examiner

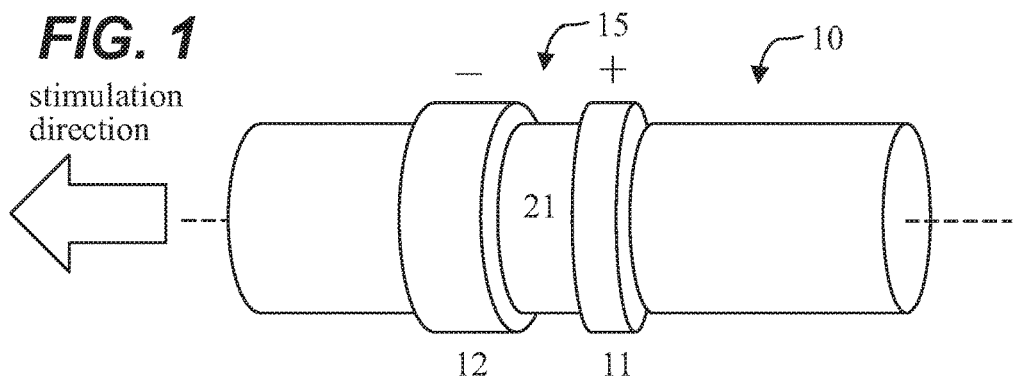
FIG. 1
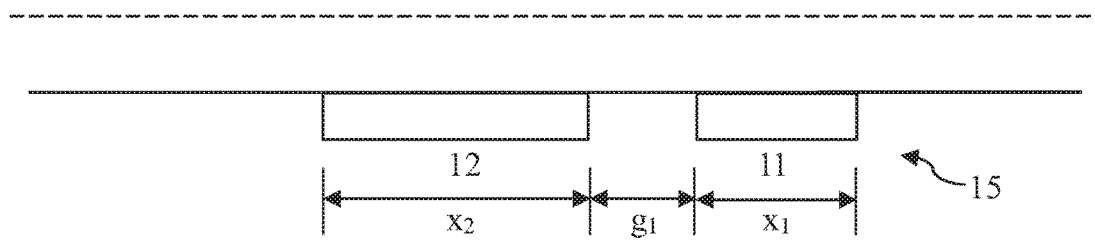
FIG. 2
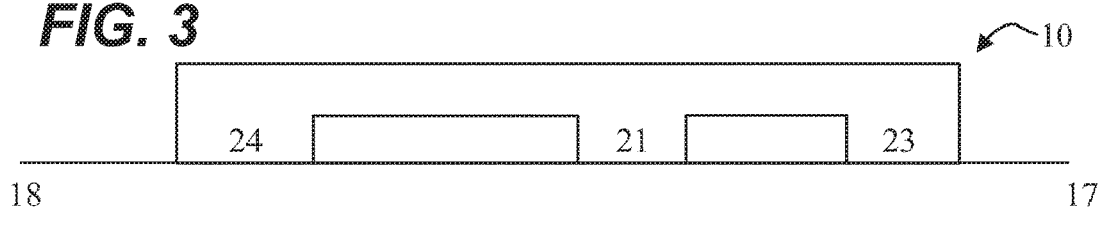
FIG. 3
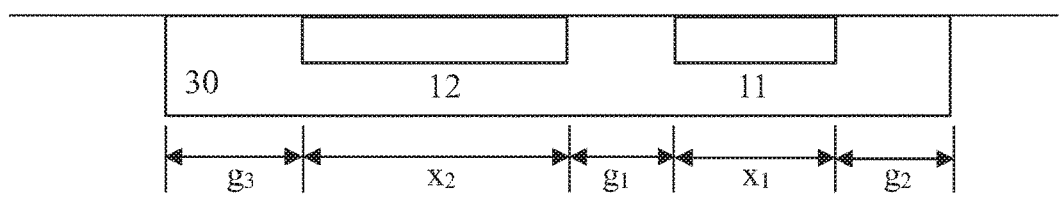
FIG. 4
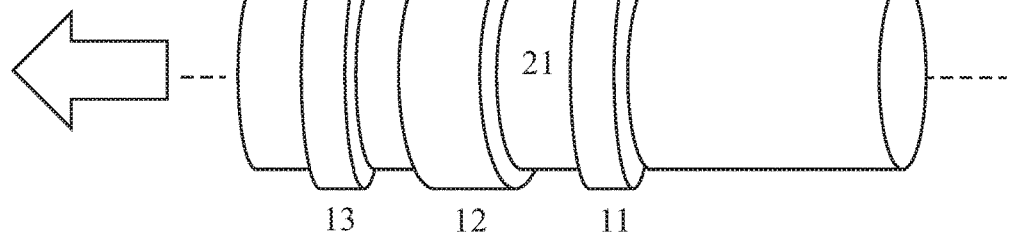

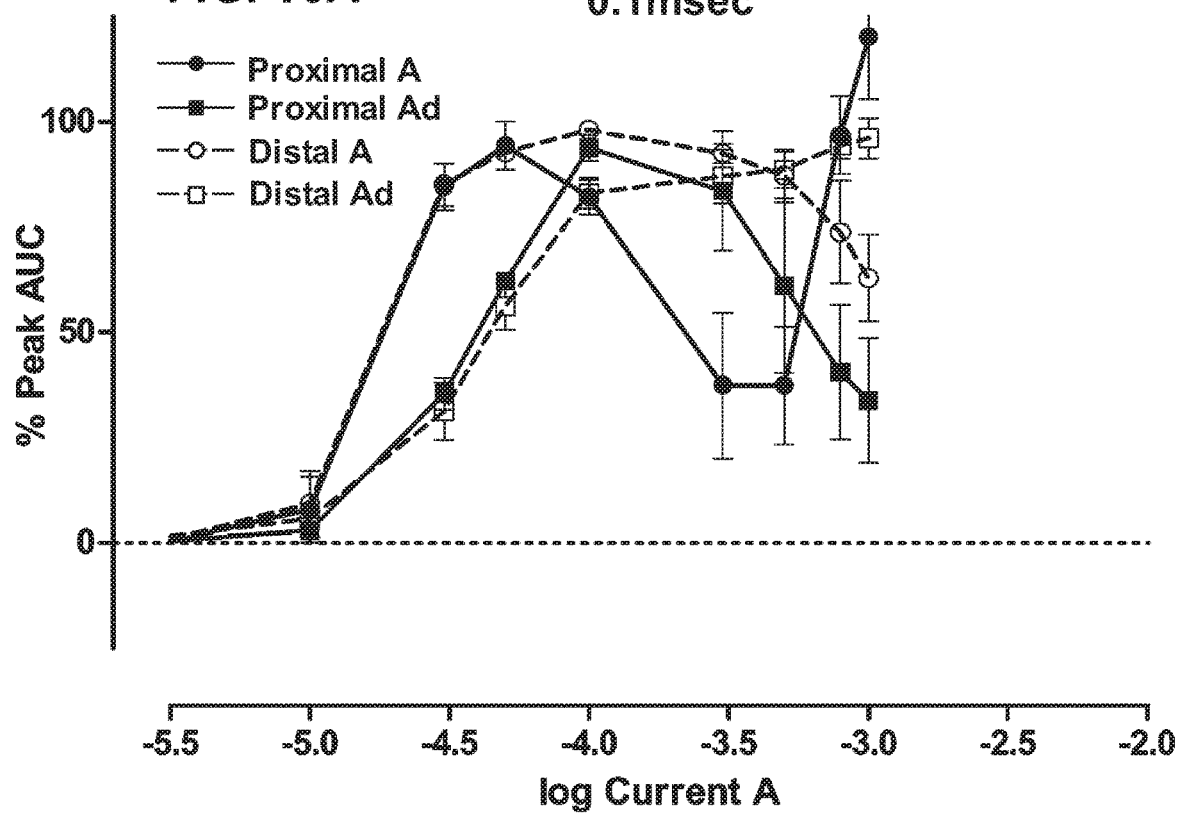
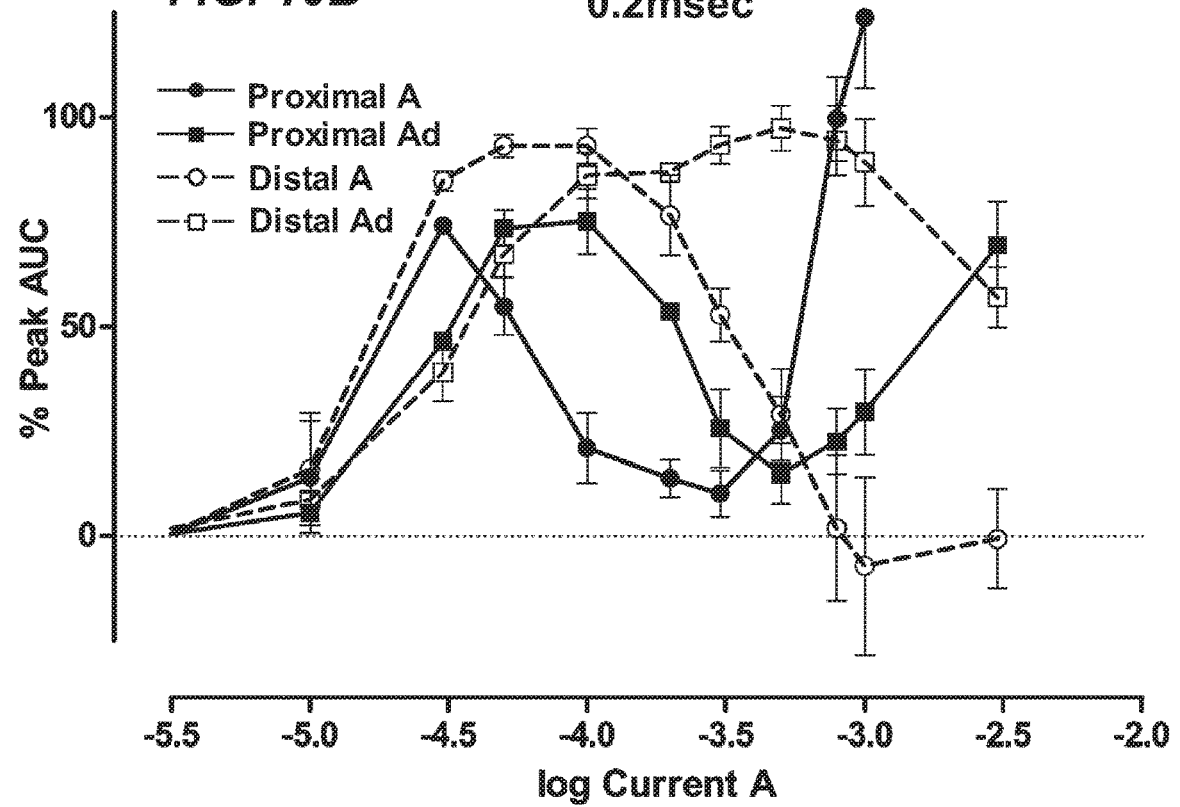

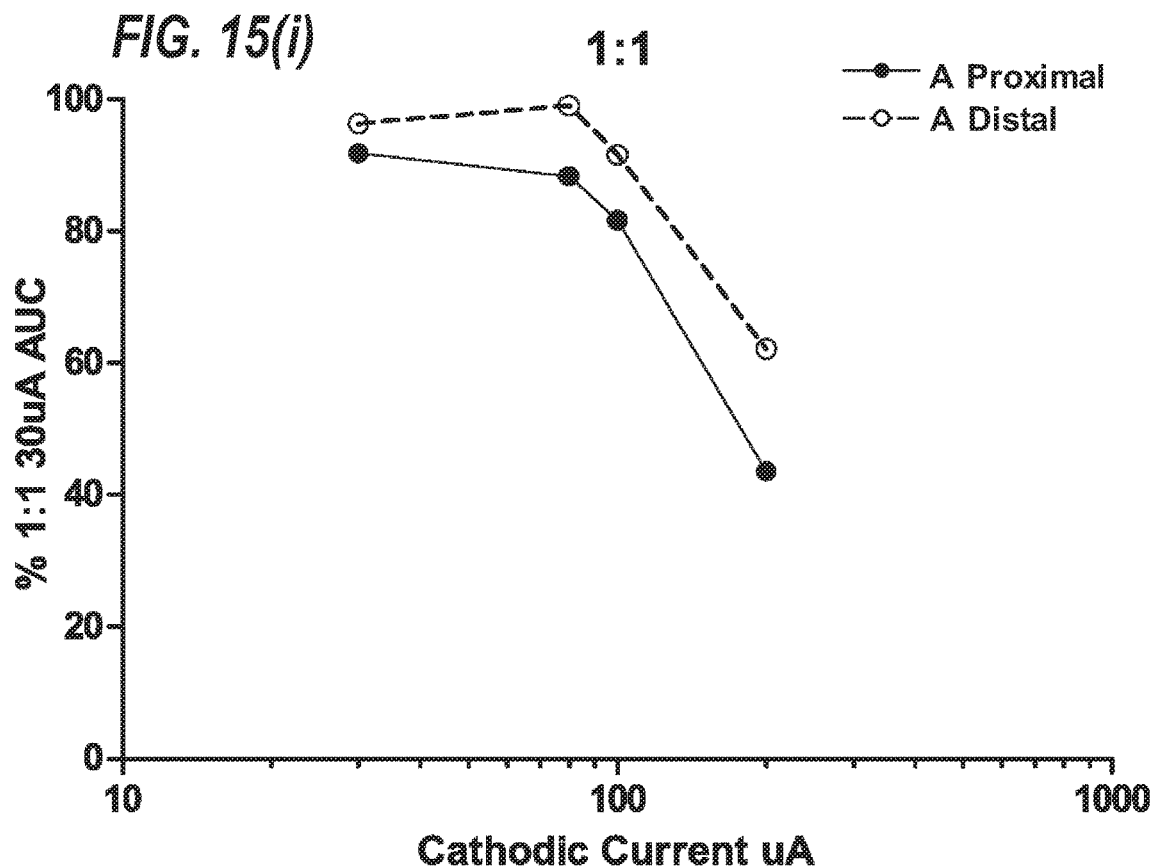
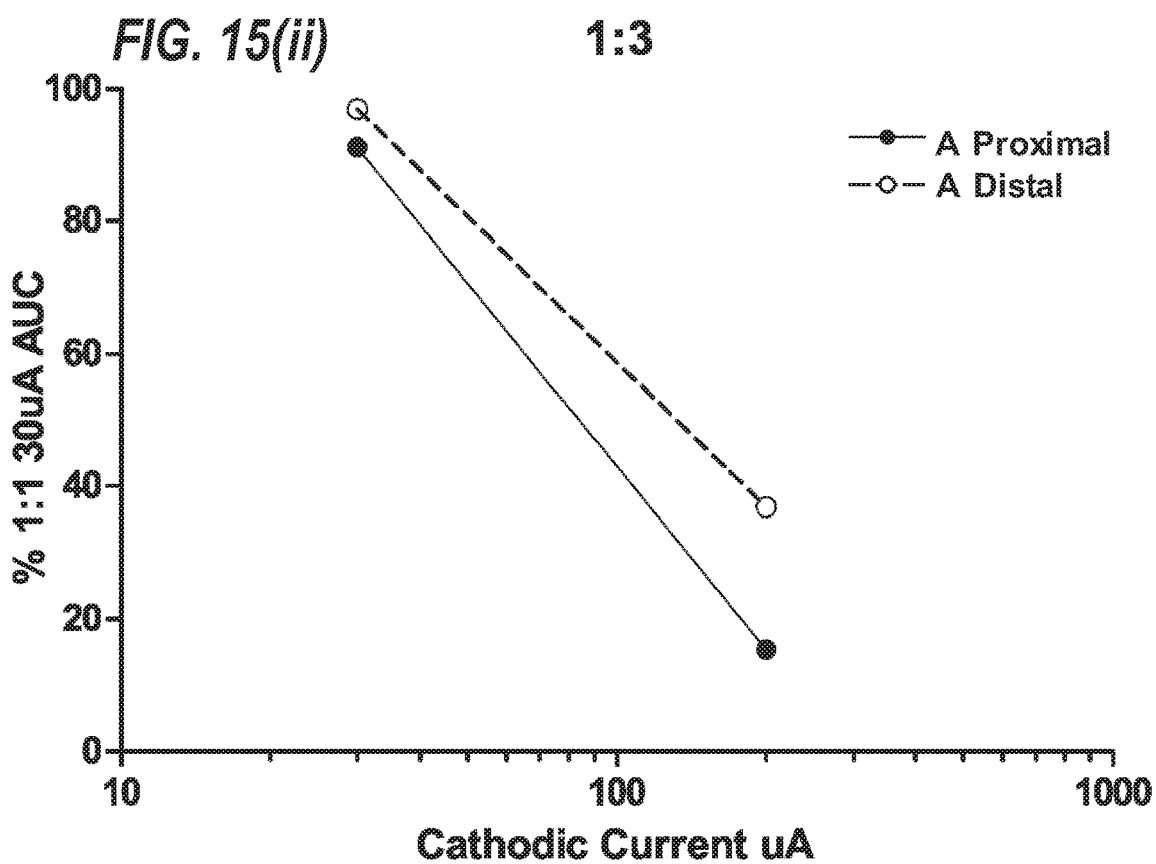

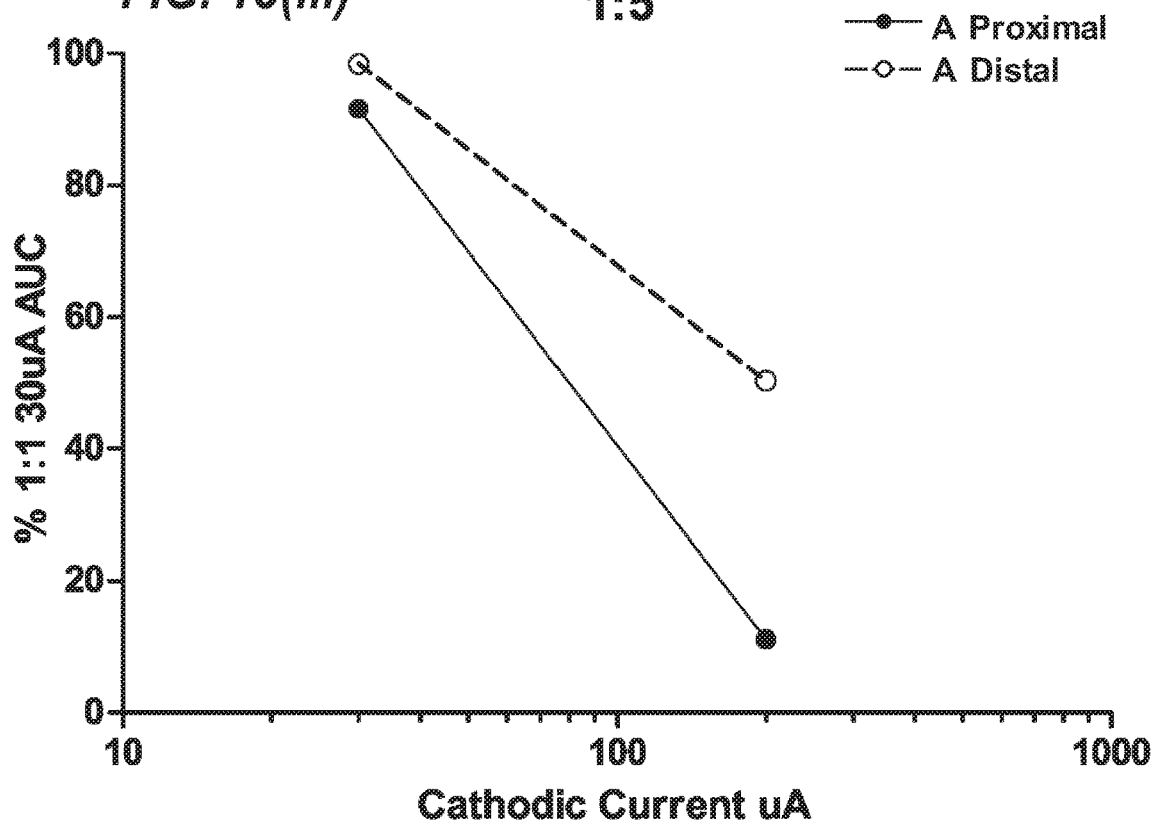
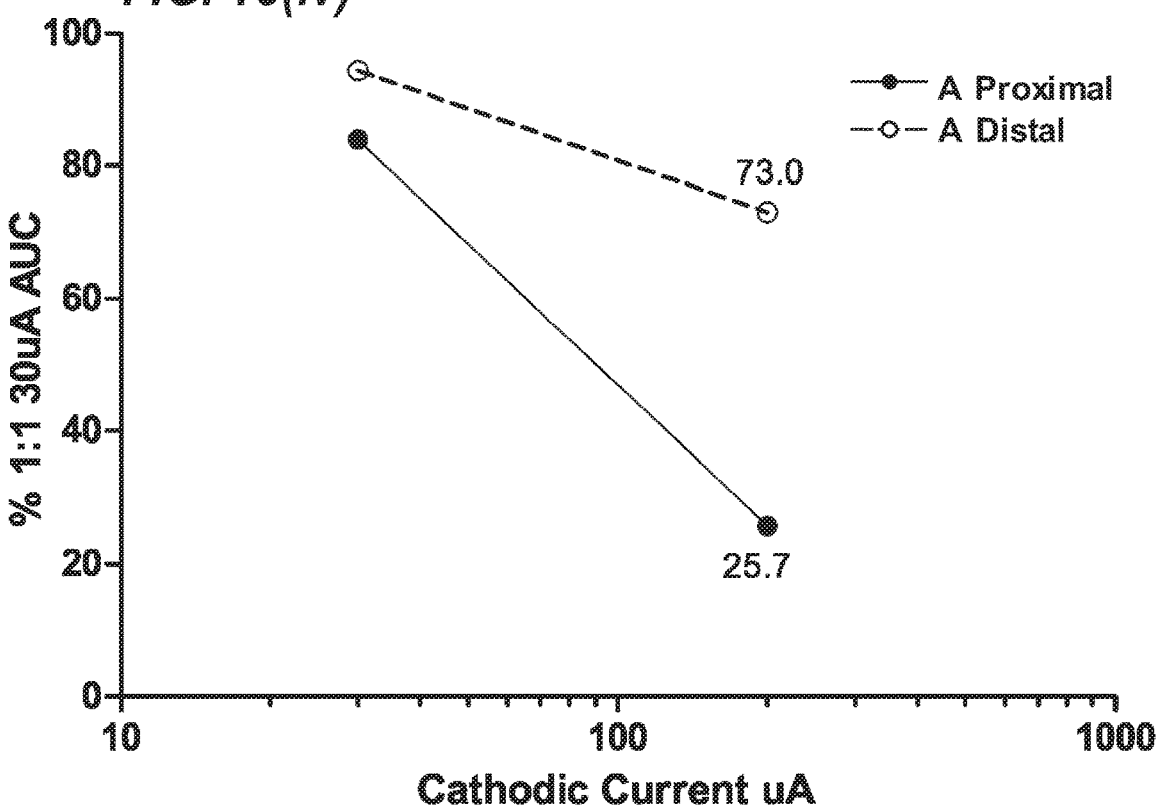

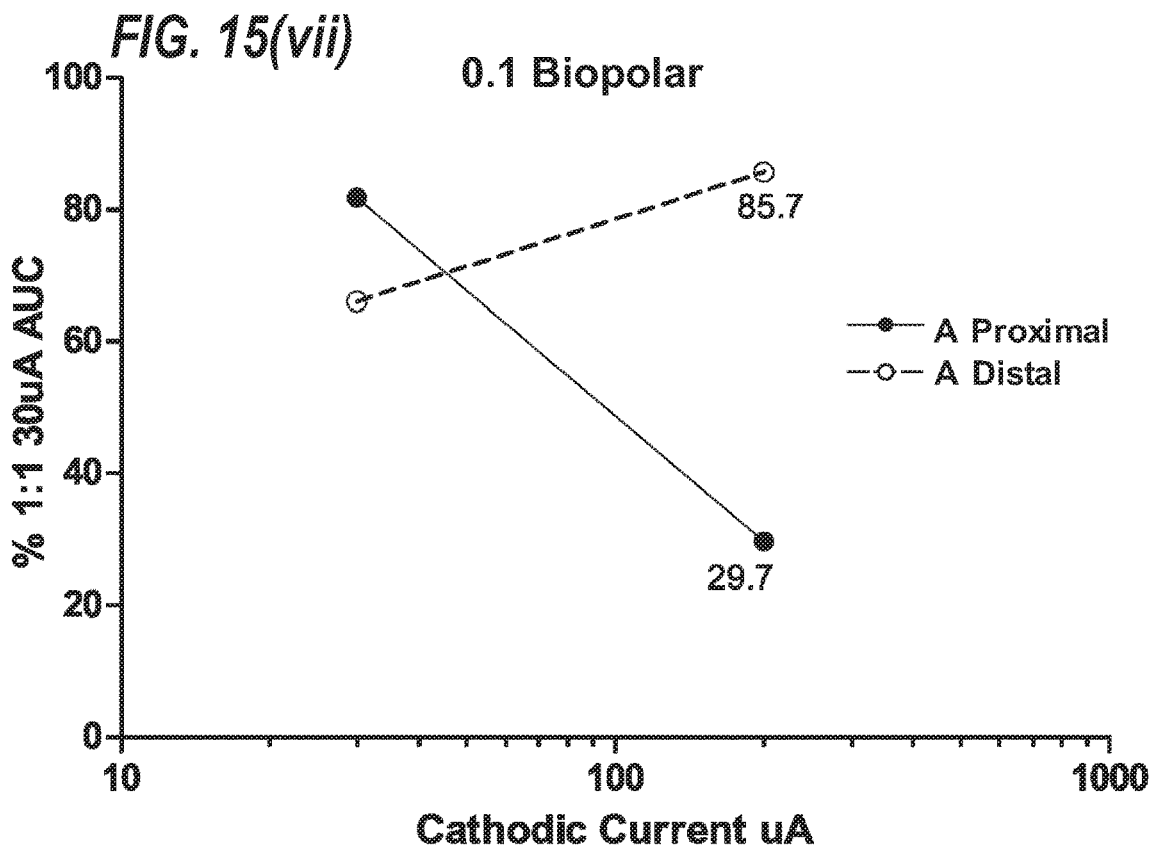
FIG. 15(vii)
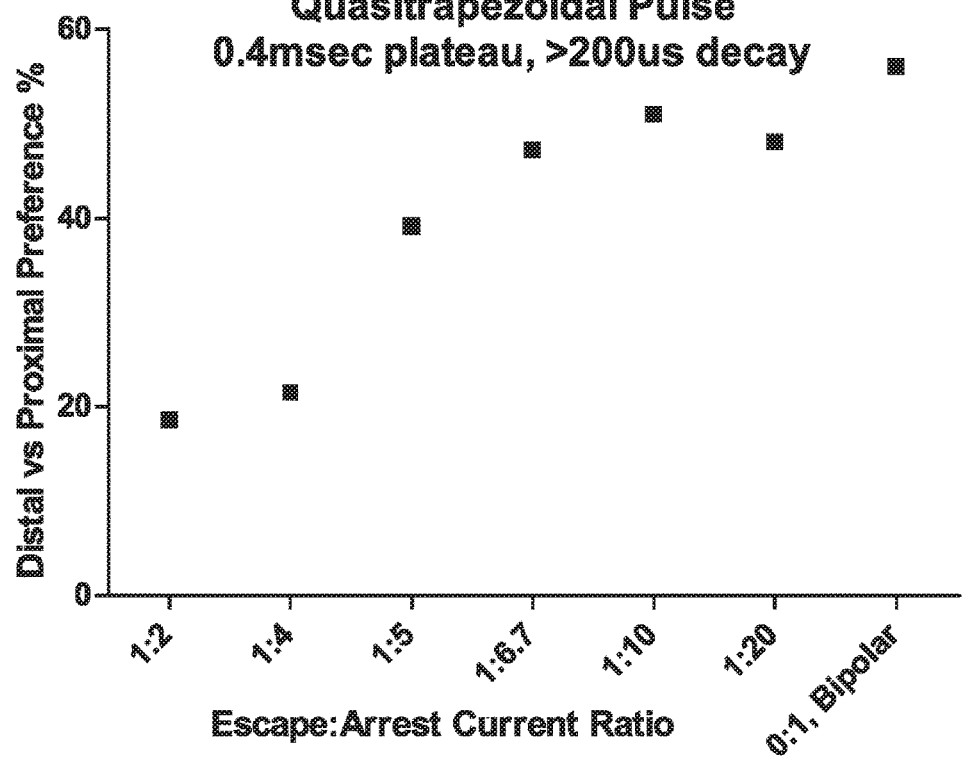
FIG. 15(viii)

BIPOLAR AND TRIPOLAR CONFIRGURATION FOR UNIDIRECTIONAL STIMULATION OF A-TYPE NERVE FIBERS

PRIORITY CLAIM

The present application is a National Phase entry of PCT Application No. PCT/GB2018/053597, filed Dec. 11, 2018, which claims priority from U.S. Provisional Application No. 62/597,227, filed Dec. 11, 2017, and U.S. Provisional Application No. 62/609,184, filed Dec. 21, 2017, each of which is hereby fully incorporated herein by reference.

TECHNICAL FIELD

This disclosure relates to stimulation of neural activity in A-type nerve fibers or at least partially myelinated fibers. More specifically, this disclosure relates to devices and systems that interface A-type nerve fibers or at least partially myelinated fibers and cause unidirectional stimulation of neural activity.

BACKGROUND

A-type nerve fibers are relatively large-size nerve fibers in the body. These fibers are myelinated, which means they carry neural activity around the body at a relatively high conduction velocity. Artificial stimulation of neural activity in A-type nerve fibers is known to be useful for treating and/or preventing various diseases in a subject. For example, artificial stimulation of neural activity in A-type nerve fibers can be used in cases of therapy for epilepsy or organ dysfunction, for instance in immunomodulation and rheumatoid arthritis treatment. Electrical devices of various shapes and sizes including one or more electrodes have been used for artificial stimulation of neural activity for years.

Unidirectional stimulation of neural activity, that is artificially-stimulated neural activity which only propagates along the nerve in one direction, can be advantageous over non-unidirectional stimulation because it may be used for collision blocking of baseline neural activity, or to reduce off-target effects, etc.

Unidirectionality can be achieved by stimulating neural activity in both directions along a nerve, and then impeding the neural activity in one direction. This typically requires an electrical device with either a cathode or an anode (i.e. a bipolar electrode arrangement), or a cathode and two anodes, one anode either side the cathode (i.e. a tripolar electrode arrangement), and a means for causing a charge density differential between the cathode and the anode(s).

For example, in "An asymmetric two electrode cuff for generation of unidirectional propagated action potentials", IEEE Transactions on Biomedical Engineering, Vol. 33, Pages 541-549, 1986, the authors describe that unidirectional stimulation can be achieved using a bipolar electrode arrangement with one recessed electrode. The cathode is radially recessed away from the nerve to reduce extracellular potential under the cathode in comparison to the extracellular potential under the anode. However, such a design may not be suitable for long-term implantation because movement of the nerve relative to the electrode arrangement may affect the ability of the device to induce unidirectional stimulation of neural activity.

In "Generation of unidirectionally propagated action potentials in a peripheral nerve by brief stimuli", Science, Vol. 206, No. 4424, Pages 1311-2, the authors report the use of a dual current source with a tripolar electrode arrangement to create a charge density differential between the cathode and anodes. Similarly, U.S. Pat. No. 7,561,922 describes a tripolar electrode configuration for unidirectional stimulation with current differentials being supplied to the cathode and anodes. However, multiple current sources can be difficult to implement in a stimulation device for nerve fibers due to restricted space available for implants.

In "A technique for collision block of peripheral nerve: single stimulus analysis", IEEE Transactions on Biomedical Engineering, Vol. BME-28, No. 5, May 1981, the authors vary the spacing between identical electrodes in a tripolar electrode configuration to generate unidirectional stimulation of neural activity in myelinated nerve fibers. The tripolar electrode comprises a cathode surrounded by two anodes. If both anodes carry equal current, by symmetry when a block occurs in one direction, it will occur in both directions. This can be mitigated by reducing the amount of current flowing through one of the anodes and spacing it further from the cathode. However, this causes a virtual cathode to arise distal to the insulator, and thus precision is required to ensure that it remains below a threshold, which imposes a limitation on the system.

Therefore, there exists a need for improved devices and systems that can provide unidirectional stimulation of A-type nerve fibers.

SUMMARY

The inventors found that adapting the surface area of the electrodes in a bipolar electrode arrangement, and optionally adapting the distance between said electrodes, leads to preferentially unidirectional stimulation of neural activity in A-type nerve fibers or at least partially myelinated fibers. The inventors also found suitable pulse widths to achieve preferentially unidirectional stimulation for the electrical signal applied to the nerve via the electrode arrangement.

A pulse width refers to a width (or time duration) of a primary phase of the waveform. In some cases where a pulse comprises a first phase that is the primary phase and a second phase which is the recovery phase, for example an anodic and/or a cathodic phase, the pulse width refers to a width (or duration) of the first phase. A pulse duration refers to the time duration during which the pulse is applied or delivered for. This may also be referred to as a stimulation time.

The inventors found that adapting the surface area of the electrodes in a tripolar electrode arrangement, and optionally adapting the distance between said electrodes, leads to preferentially unidirectional stimulation of neural activity in A-type nerve fibers or at least partially myelinated fibers. The inventors also found suitable pulse widths to achieve preferentially unidirectional stimulation for the electrical signal applied to the nerve via the electrode arrangement.

In general, electrically induced compound action potentials are generated if the depolarization under the cathode is sufficient to increase local membrane potentials past the activation threshold for voltage-gated sodium channels from the resting membrane potential. The activation threshold is typically around −40 mV, and the resting membrane potential is typically around −70 mV. Thus, the difference between the activation threshold and the resting membrane potential is around $\Delta 30$ mV.

Once the activation threshold is passed and the NaV channels (also known as "voltage-dependent" sodium channels) are opened, positively charged sodium ions flow down their concentration gradient into the cell until reaching their reversal potential (which is typically around +50 mV). This local influx of positively charged sodium ions, which is the first phase of the action potential, initiates a wave of depolarization in both directions along the axon axis, opening adjacent NaV channels, thus propagating an action potential in both directions. This wave of depolarization can locally be greater than ~Δ100 mV (resting membrane potential to reversal potential), but likely less due to passive diffusion between nodes of Ranvier. In order to arrest this propagation at a second point along the axon axis, electrical hyperpolarization, via a positively charged anode, must be employed to reduce the resting membrane potential ($E_{rest}$=−70 mV) to a point that the incoming wave of depolarization (~Δ100 mV) is insufficient to reach the threshold potential ($E_{thres}$=−40 mV). Therefore for arrest to occur, the resting membrane potential would need to be hyperpolarized by −70 mV from the previous resting state. This is illustrated in following equation:

$$\Delta 100 \text{ mV} - (E_{thres} - E_{rest}) = 100 \text{ mV} - (-40 \text{ mV} - (-70 \text{ mV})) = -70 \text{ mV} = \Delta 70 \text{ mV hyperpolarization}$$

Therefore, the electrode charge density required to generate an action potential (i.e. to induce ~Δ30 mV depolarization to threshold) is always lower than the charge density required to arrest an action potential (induce ~Δ70 mV hyperpolarization) when the anode and cathode have the same surface area. When using anode or cathode pairs with symmetric surface area, charge density for a given current injection will be equal and opposite on each electrode. This will generate a bell shaped activation/arrest profile as charge density and current increase.

By introducing surface area differences between the electrodes in the pair, one can concentrate or reduce charge on any given electrode. When reducing the anode surface area compared to the cathode, charge density is increased under the anode for any given current injection compared to the cathode. This allows arrest to occur at lower currents than can be achieved in electrodes with equal surface areas. In conjunction, this surface area differential reduces cathodal charge density for a given current injection. This shifts activation to higher currents. The reduction of block current threshold due to anode surface area reduction and increase in activation current threshold due to cathode surface area increases can together result in a convergence of block and activation with the same current.

The disclosure provides a neural interface device for unidirectional stimulation of a nerve comprising at least one A-type nerve fiber or comprising at least one at least partially myelinated fiber. The device comprises an electrode arrangement configured to be placed on or around the nerve. The electrode arrangement comprises at least a first electrode having a first surface area, and configured to be positively charged and a second electrode having a second surface area configured to be negatively charged, and spaced apart from the first electrode so as to define a first gap along the longitudinal axis of the nerve. The second surface area (of the second electrode) is larger than the first surface area (of the first electrode). In some embodiments, the second surface area is three times as large as the first surface area. The first surface area and the second surface area may be arranged to communicate electrically with the nerve, when the device is placed on or around the nerve. The electrical communication between the electrodes' surface areas and the nerve allows an electrical signal to be imparted upon the nerve. This may involve a direct or an indirect physically connection.

The first electrode may have a first width, and the second electrode may have a second width. The width of the second electrode in the direction of the longitudinal axis of the nerve when the neural interface device is placed around the nerve can be at least three times the width of the first electrode. Indeed, the width of the second electrode may be approximately (or exactly) twice the width of the first electrode, approximately (or exactly) three times the width of the first electrode, approximately (or exactly) four times the width of the first electrode, or approximately (or exactly) five times the width of the first electrode. These electrode configurations may be advantageous for alleviating at least some of the issues identified above in respect of known arrangements.

By introducing surface area differences between the electrodes in the (tripolar) electrode configuration, one can concentrate or reduce charge on any given electrode. When reducing the anode surface area compared to the cathode, charge density is increased under the anode for any given current injection compared to the cathode. This allows arrest to occur at lower currents than can be achieved in electrodes with equal surface areas. In conjunction, this surface area differential reduces cathodal charge density for a given current injection. This shifts activation to higher currents. The reduction of block current threshold due to anode surface area reduction and increase in activation current threshold due to cathode surface area increases can together result in a convergence of block and activation with the same current.

The disclosure provides a neural interface device for unidirectional stimulation of a nerve comprising at least one A-type nerve fiber or comprising at least one at least partially myelinated fiber. The device comprises an electrode arrangement configured to be placed on or around the nerve. The electrode arrangement comprises at least a first electrode having a first surface area, and configured to be positively charged and a second electrode having a second surface area configured to be negatively charged, and spaced apart from the first electrode so as to define a first gap along the longitudinal axis of the nerve. The device further comprises a third electrode having a third surface area, and configured to be positively charged and spaced apart from the second electrode so as to define a second gap along the longitudinal axis of the nerve. The first electrode is adjacent the second electrode, and the third electrode is adjacent the second electrode with the second electrode positioned in between the first electrode and the second electrode.

The second surface area (of the second electrode) may be larger than the first surface area (of the first electrode). The second surface area (of the second electrode) may be larger than the third surface area (of the third electrode). The second surface area (of the second electrode) may be larger than both of the surface areas of the first and third electrode respectively.

In some embodiments, the second surface area is two times as large as the first surface area. In some embodiments, the second surface area is two times as large as the third surface area.

The first surface area, the second surface area and the third surface area may be arranged to communicate electrically with the nerve, when the device is placed on or around the nerve. The electrical communication between the electrodes' surface areas and the nerve allows an electrical signal to be imparted upon the nerve. This may involve a direct or an indirect physically connection.

The first electrode may have a first width, the second electrode may have a second width and the third electrode may have a third width. The width of the second electrode in the direction of the longitudinal axis of the nerve when the neural interface device is placed around the nerve can be the sum of the width of the first electrode (i.e. the first width) and the width of the third electrode (i.e. the third width). In another example, the width of the second electrode (i.e. the second width) is two times the first width or the third width. The first and the third widths may be the same. In another example, the widths of each of the first, second and third electrodes are the same.

Indeed, the width of the second electrode may be approximately (or exactly) twice the width of the first electrode, approximately (or exactly) three times the width of the first electrode, approximately (or exactly) four times the width of the first electrode, approximately (or exactly) five times the width of the first electrode, or approximately (or exactly) ten times the width of the first electrode. These electrode configurations may be advantageous for alleviating at least some of the issues identified above in respect of known arrangements.

The width of the second electrode in the direction of the longitudinal axis of the nerve when the neural interface device is placed around the nerve can be three times the width of the third electrode. Indeed, the width of the second electrode may be approximately (or exactly) twice the width of the third electrode, approximately (or exactly) three times the width of the third electrode, approximately (or exactly) four times the width of the third electrode, approximately (or exactly) five times the width of the third electrode, or approximately (or exactly) ten times the width of the third electrode. These electrode configurations may be advantageous for alleviating at least some of the issues identified above in respect of known arrangements.

Specifically, the electrode configurations of the present disclosure allow efficacious treatment to be provided, but with a reduced current to achieve block compared to bipolar electrodes with equal surface area. A reduced current can, for instance, reduce the likelihood of nerve damage and side effects, as well as using energy more efficiently. Energy efficiency may be particularly important in situations in which the implantable device is used in conjunction with a portable energy source, such as a battery.

The configuration in which the second electrode is three times the width of the first electrode and/or third electrode (or, in other words, where the surface area of the second electrode is three times as large as the surface area of the first/third electrode) has been found to be particularly advantageous, specifically for providing a stimulation signal with reduced current. In essence, with a given current coupled between the first electrode (e.g. anode) and the second electrode (e.g. cathode) and coupled between the second electrode and the third electrode, the charge density will be concentrated on the first and/or third electrodes more so than on the second electrode, when the surface area of the second electrode is larger than the first electrode. Thus, the ratio of the second electrode surface area to the first electrode surface area ratio allows a reduced current to be provided to achieve a block. It has been found that an increased second electrode surface area to first electrode surface area ratio can be advantageous. A ratio of 3 was found to be particularly advantageous and ratios up to 5 were found to be particularly advantageous in some embodiments.

The disclosure also provides a system for unidirectional stimulation of a nerve comprising at least one A-type nerve fiber or at least one at least partially myelinated fiber. The nerve may be, for instance, the vagus nerve, somatic nerves, the cervical nerve or any at least partially myelinated peripheral nerve. Thus, the system can allow treatment of disease through autonomic nerves, sensory nerves or nerves for somatic motor control. The device and system described herein can also allow selective stimulation of fibers with a higher activation threshold by creating a bidirectional block of A-fibers.

The system can be used for A-type nerve fibers, as well as for B-type nerve fibers (which have similar conduction velocities and may include Aδ-type nerve fibers). Typically, A-type nerve fibers have a conduction velocity greater than around 8-10 m/s. Typically, B-type and Aδ-type nerve fibers have a conduction velocity less than around 8-10 m/s, but greater than 3 m/s.

The system comprises one or more neural interface devices of the disclosure and a voltage or current source which is electrically connected to the electrode arrangement of the neural interface device, wherein the voltage or current source is configured to generate an electrical signal to be applied to the nerve via the electrode arrangement.

The disclosure also provides a method for unidirectional stimulation of a nerve comprising at least one A-type nerve fiber. The method comprises providing one or more neural interfaces of the disclosure, and generating an electrical signal to be applied to the nerve via the electrode arrangement by least one voltage or current source electrically connected to the electrode arrangement.

The disclosure also provides a computer program comprising code portions which, when loaded and run on a computing device, cause the computing device to generate an electrical signal to be applied to the nerve via the electrode arrangement of a neural interface device of the disclosure and at least one voltage or current source electrically connected to the electrode arrangement. Also provided is a computer-readable medium having stored thereon the computer program.

The disclosure also provides a modified nerve to which the neural interface device or the system of the disclosure is attached. The electrode arrangement of the neural interface device is in signaling contact with the nerve so the nerve can be distinguished from the nerve in its natural state. In some embodiments the nerve comprises a plurality of A-type nerve fibers.

The devices and systems described herein can also allow selective stimulation of fibers with a higher activation threshold by creating a bidirectional block of A-fibers.

BRIEF DESCRIPTION OF THE DRAWINGS

Embodiments of the disclosure will be described, by way of example, with reference to the following drawings, in which:

FIG. 1 illustrates a neural interface device with two electrodes.

FIG. 2 illustrates a cross-section of a neural interface device with two electrodes.

FIG. 3 illustrates a neural interface device with two electrodes and a flexible non-conductive layer.

FIG. 4 illustrates a neural interface device with three electrodes.

FIGS. 10A-D illustrate action potential propagation distal and proximal to a central electrode array when the electrode configuration of FIG. 7 is stimulated in a bipolar manner with a quasitrapezoidal pulse.

DETAILED DESCRIPTION

Figure 5:
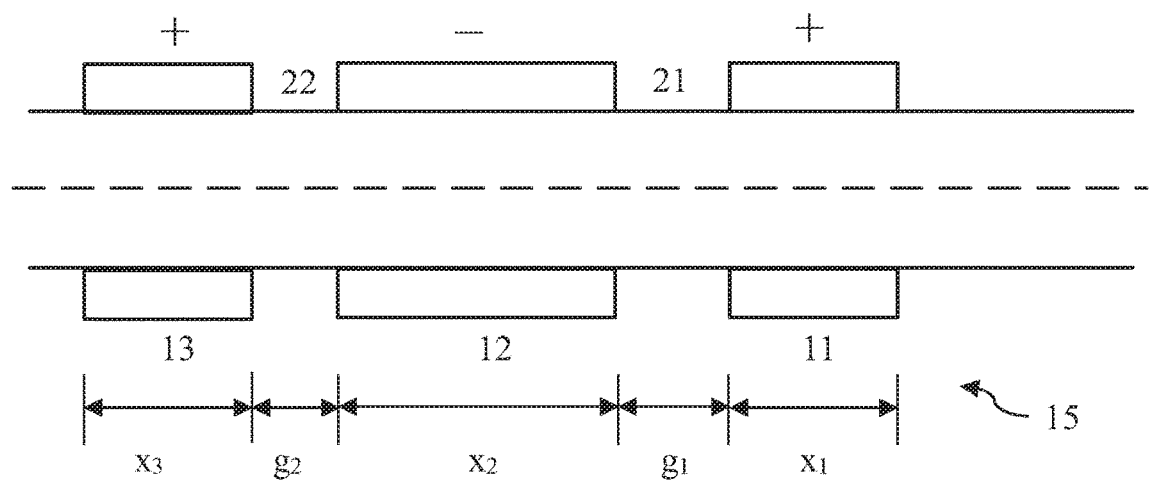
FIG. 5 illustrates a cross-section of a neural interface device with three electrodes.

A nerve fiber is a thread like extension of a neuron, which is formed by an axon and the axon covering. The axons of some nerve fibers, including A-type fibers which are the focus of this disclosure, are typically covered by an insulating layer known as myelin. These nerve fibers are referred to as myelinated or medullated nerve fibers. Nerve fibers including C-type fibers which do not have a myelin sheath are referred to as unmyelinated, non-myelinated or non-medullated nerve fibers.

Myelin prevents action potentials, which are electrical signals that travel along axons, from decaying due to electrical current leaking out through the axonal membrane. Myelinated axons thus conduct action potentials more quickly than unmyelinated axons. For instance, the conduction velocity of action potentials in vagal A-type sensory nerve fibers is typically >10 m/s, whereas the conduction velocity in unmyelinated (i.e. C-type) nerve fibers is typically <2 m/s. As will be discussed below, the higher conduction velocity in myelinated fibers can be exploited in the design of a device for unidirectional stimulation of neural activity.

The myelin covering in a myelinated nerve is arranged on the nerve fiber as a series of individual sheaths positioned along the nerve, each of which circumvents the nerve fiber. Gaps, referred to in the art as nodes of Ranvier, are formed along the nerve between each of the myelin sheaths.

Thus, a myelinated nerve, as referred to herein, may comprise a plurality of individual myelin sheaths along the nerve which circumvent the nerve fiber. A gap between an adjacent pair of myelin sheaths may define a node of Ranvier.

Myelinated nerves include Type I, II, and III sensory fibers (corresponding to Aα-, Aβ- and Aδ-type nerve fibers using Erlandger-Gasser classification) and preganglionic fibers (corresponding to B-type nerve fibers using Erlandger-Gasser classification). Type I sensory fibers typically have a diameter between 13 and 20 μm and a conduction velocity of action potentials in the region of 80 to 120 m/s. Type II sensory fibers typically with a diameter between 6 and 12 μm and a conduction velocity of action potentials in the region of 33 to 75 m/s.

Type III sensory fibers are different from Type I and II sensory fibers in that the myelin covering is far thinner and the diameter of the nerve fiber is much narrower for Type III sensory fibers in comparison to Type I and II sensory fibers. This results in a slower conduction velocity for action potentials in Type III sensory fibers than in Type I and II sensory fibers, but faster than in an unmyelinated nerve. For this reason, Type III sensory fibers are sometimes referred to as mixed fibers. Typically, the diameter of a Type III sensory fiber is 1 to 5 μm and the conduction velocity is greater than 3 m/s but less than around 8-10 m/s.

A-type nerve fibers also have a larger diameter than unmyelinated (i.e. C-type) fibers, typically in the region of 6 to 20 μm.

As discussed above, there exists a need to provide a device which is capable of stimulating A-type nerve fibers (or myelinated fibers) with an efficacious signal for treatment of various ailments, but with a reduced current from paired electrodes.

Unidirectional Stimulation

Stimulation of neural activity, as used herein, is when the neural activity of the nerve is increased from the baseline neural activity. Unidirectional stimulation thus refers to when neural activity of the nerve is increased from the baseline neural activity in one direction along the longitudinal axis of the nerve. It is known that both stimulation and directional stimulation of neural activity can be achieved by applying an electrical signal to the nerve.

Neural activity of a nerve is the signaling activity of the nerve, for example the amplitude and/or frequency of action potentials in the nerve. When the nerve comprises a plurality of A-type nerve fibers, such as in the present disclosure, the signaling activity of each of the nerve fibers is summed to determine a compound action potential at a cross-section of the nerve fiber bundle.

When a functioning nerve fiber is in a normal state, at any point along the axon, the nerve fiber will have a distribution of potassium and sodium ions across the nerve membrane. The distribution at one point along the axon determines the electrical membrane potential of the axon at that point, which in turn influences the distribution of potassium and sodium ions at an adjacent point, which in turn determines the electrical membrane potential of the axon at that point, and so on. This is a nerve fiber operating in its normal state, wherein action potentials propagate from point to adjacent point along the axon, and which can be observed using conventional experimentation.

One way of characterizing stimulation of neural activity is a distribution of ions at one or more points in/around the axon which is created not by virtue of the electrical membrane potential at adjacent points of the nerve as a result of a propagating action potential, but by virtue of the application of a temporary external electrical field. The temporary external electrical field artificially modifies the distribution of ions within/around a point in the nerve fiber, causing depolarization of the nerve membrane that would not otherwise occur. The depolarization of the nerve membrane caused by the temporary external electrical field gives rise to two de novo action potentials which propagate in opposite directions along the nerve fiber from the point of the temporary external electrical field.

This is a nerve fiber operating in a disrupted state, which can be observed by a distribution of potassium and sodium ions at a point in the axon (the point where a temporary external electric field is applied) that has an electrical membrane potential that is not influenced or determined by the electrical membrane potential of an adjacent point.

Stimulation of neural activity in a nerve is thus understood to be increasing neural activity of the nerve fibers from the point of cathodal electrical signal application. Thus, the nerve at the point of signal application is modified in that the nerve membranes are reversibly depolarized by an electric field, such two de novo compound action potentials are generated. Moreover, the nerve past the point of signal application in both direction along the nerve is modified in that the two de novo compound action potentials propagate in opposite directions along the nerve.

In directional stimulation, one of the two de novo compound actions potentials generated by the temporary external electrical field is impeded such that en masse propagation along the nerve is reduced or arrested completely. As a result, a de novo compound action potential propagates in along the nerve more robustly or completely in one direction over the other.

Neural activity can be impeded by applying an electrical signal to the nerve at a second point.

The nerve at the second point of signal application is modified in that the nerve membranes are hyperpolarized by the temporary external electric field of the further electrical signal, such that a compound action potential does not propagate through the modified nerve. Hence, the nerve at the second point of signal application is modified in that it has lost its capacity to propagate compound action potentials, whereas the portions of the nerve before and after the point of signal application have the capacity to propagate compound action potentials.

Disclosed herein are devices, systems and methods that preferentially cause such unidirectional stimulation of neural activity in a nerve comprising at least one or a plurality of A-type nerve fibers (or at least one or a plurality of at least partially myelinated fibers) by applying an electrical signal to the nerve. The nerve may be, for instance, the vagus nerve. Suitable electric signals for use in the devices, systems and methods are also disclosed.

Neural Interface Device (FIGS. 1 to 3)

A neural interface device 10 according to the disclosure is a device that is in physical contact with a nerve, where the nerve comprises a plurality of A-type nerve fibers. When an electrical signal is applied to the nerve via the neural interface device 10, the neural interface device 10 causes unidirectional stimulation of neural activity in the nerve, such as the vagus nerve in a human or an animal subject.

With reference to FIG. 1, the neural interface device 10 comprises an electrode arrangement 15. The electrode arrangement 15 is configured to be placed on or around the nerve when the neural interface device 10 is in use. The electrode arrangement 15 includes a plurality of electrodes which are spaced apart from each other so as to define a gap between each of the electrodes, where the gap is positioned along the longitudinal axis of the nerve (i.e. in the direction of the longitudinal axis of the nerve). In particular, the electrode arrangement 10 of FIG. 1 includes a first electrode 11 and a second electrode 12 separated by a first gap 21. This electrode arrangement is referred to as a bipolar electrode arrangement.

The first electrode 11 and the second electrode 12 can be cuff type electrodes (for example, spiral cuff, helical cuff or flat interface) which at least partially circumvent the nerve. For example, the first electrode 11 and the second electrode 12 shown in FIG. 1 are flat interface cuff electrodes which fully circumvent the nerve. However, other types of electrodes known in the art are also suitable for use in the electrode arrangement 15. For instances, one or more of flat interface electrodes, mesh electrodes, linear rod-shaped lead electrodes, paddle-style lead electrodes, disc contact electrodes, hook electrodes, sling electrodes, intrafascicular electrode, glass suction electrodes, paddle electrodes, and percutaneous cylindrical electrodes may be used It will be appreciated that any suitable type of electrode could be used, which may be one of the examples disclosed herein but not limited thereto.

The first electrode 11 and second electrode 12 may fabricated from, or be partially or entirely coated with, a high charge capacity material such as platinum black, iridium oxide, titanium nitride, tantalum, poly(elthylene-dioxythiophene) and suitable combinations thereof, such as platinum-iridium alloy.

The surface area of each of the first electrode 11 and the second electrode 12 which is in contact with the nerve is specially adapted for unidirectional stimulation. In particular, the first electrode 11 has a first surface area and the second electrode 12 has a second surface area, and the second surface area is larger than the first surface area.

In an electrode arrangement 15 which uses cuff type electrodes that fully circumvent the nerve, the size of this surface area can be calculated by multiplying 7C (i.e. 3.14159) by the internal diameter and width of the respective electrode (i.e. the first electrode 11 or the second electrode 12). Since the internal diameter of the first electrode 11 and the second electrode 12 is fixed by the diameter of the nerve, the surface area of each of the first electrode 11 and the second electrode 12 in contact with the nerve is adjusted by changing the width of the electrode. In one example, the internal diameter of the first and second electrodes may be 0.5 mm.

The width of each of the first electrode 11 and the second electrode 12 is defined as the distance the electrode spans along the longitudinal axis of the nerve. In FIG. 2, the width of the first electrode 11 is denoted $x_1$, whilst the width of the second electrode is denoted $x_2$.

The width of the first electrode $x_1$ is defined by the user. The width of the first electrode $x_1$ may be around 0.3 mm.

Similarly, the width of the gap between the first electrode 11 and the second electrode 12 is defined as the distance that the gap spans along the longitudinal axis of the nerve. In FIG. 2, the width of the first gap is denoted $g_1$.

The width of the first gap $g_1$ is also defined by the user. The width of the first electrode $x_1$ is around the same size as the first electrode, which in this example is 0.3 mm.

The surface area of the second electrode 12 is adapted to be larger than the surface area of the first electrode 11. When the surface area of the second electrode 12 is larger than the surface area of the first electrode 11 this concentrates charge density under the first electrode 11 for a given current compared to charge under the second electrode 12, thus strengthening the hyperpolarization of the nerve without increased energy requirements. Thus, the width of the second electrode $x_2$ may be greater than the width of the first electrode $x_1$. For example, the width of the second electrode $x_2$ may be at least two, three, four or five times the width of the first electrode $x_1$.

In a bipolar electrode arrangement (e.g. the arrangements of FIGS. 1 and 2), the width of the second electrode $x_2$ may also be less than or equal to five times the width of the first electrode $x_1$. This is to avoid stimulating additional action potentials under the second electrode 12.

For example, the width of the second electrode $x_2$ may be one of: $2.0x_1$, $2.5x_1$, $3.0 x_1$, $3.5x_1$ $4.0 x_1$, $4.5x_1$ or $5.0x_1$. In other words, the ratio of the surface area of the second electrode to the ratio of the surface area of the first electrode may be 2 (2:1), 2.5 (5:2), 3 (3:1), 3.5 (7:2), 4 (8:2), 4.5 (9:2) or 5 (5:1).

To achieve unidirectional stimulation, the first electrode 11 is a positively charged electrode, also referred to as the "arrest anode", and the second electrode 12 is a negatively charged electrode, also referred to as the "cathode".

The nerve is stimulated by the second electrode 12 such that two compound action potentials, which propagate in opposite directions along the nerve, are generated in the nerve under the second electrode 12. Once one of the compound action potentials reaches the first electrode 11, it is impeded such that it cannot propagate along the nerve any further, leading to unidirectional stimulation from the second electrode 12 in the direction away from the first electrode 11, as shown in FIG. 1. Thus, the first electrode 11 and second electrode 12 are positioned along the nerve respectively in the direction of the unidirectional stimulation. Put another way, the second electrode 12 is at the "escape end" of the neural interface device 10, from which compound action potentials caused by applying the electrical signal may propagate. The first electrode 11, on the other hand, is at the "arrest end" of the neural interface device 10, from which compound action potentials cannot propagate.

In particular, a compound action potential is impeded by adapting the pulse width of the electrical signal applied to the nerve based on the size of the gap between the electrodes. More specifically, the width of the first gap $g_1$ between the first electrode 11 and the second electrode 12 is set so that one of the compound action potential generated in the nerve under the second electrode 12 arrives at the first electrode 11 when hyperpolarization of the nerve is present. This stops the compound action potential from propagating along the nerve any further. Suitable electrical signals and pulse widths are discussed in detail below. In one example, the width of the gap $g_1$ is 0.3 mm. Thus, the width of the gap $g_1$ may be approximately or exactly the same as the width of the first electrode $x_1$.

The width (or surface area) of the first electrode relative to the width (or surface area) of the 25 second electrode has been found to allow the device to provide an efficacious signal, while reducing the magnitude of the current required to achieve directional propagation. This advantage is explained in greater detail in the summary above.

The neural interface device 10 may further comprise a flexible non-conductive layer 30, as shown in FIG. 3. In other words, the flexible non-conductive layer 30 is an insulator. The electrode arrangement 15 may be mounted on to or otherwise attached to the flexible non-conductive layer 30. When in use, the electrode arrangement 15 interfaces the nerve and the flexible non-conductive layer interfaces the electrode arrangement 15. The flexible non-conductive layer 30 may conform to the shape of the electrodes such that it resides in the first gap 21 between the electrodes and additionally interfaces the nerve in that gap. The flexible non-conductive layer 30 may reside in a second gap 23 between the first electrode 11 and a first end 17 of the device 10, and the flexible non-conductive layer 30 may reside in a third gap 24 between the second electrode 12 and a second end 18 of the device 10.

The flexible non-conductive layer 30 may be made from a polysiloxanes (i.e. silicone) or a similar material to allow the flexible non-conductive layer to conform to the shape of the nerve. In some embodiments, the flexible non-conductive 30 layer is configured to at least partially circumvent the nerve when in use. The flexible non-conductive layer 30 may fully circumvent the nerve, as shown in FIG. 3.

The flexible non-conductive layer may form a cuff around the nerve. The cuff may be fastened in place on the nerve using any means known in the art. The cuff has two open ends which are perpendicular to the longitudinal axis of the nerve. The first open end 17 and second open end 18 of the cuff are shown in FIG. 3.

A second gap 23 is defined as the gap along the longitudinal axis of the nerve between the first open end 17 and the first electrode 11. The second gap 23 defines a first non-conductive portion.

Similarly, a third gap 24 is defined as the gap along the longitudinal axis of the nerve between the second open end 18 and the second electrode 12 in a bipolar electrode arrangement (shown in FIG. 3). The third gap 24 defines a second non-conductive portion. As shown in FIG. 3, the width of the second gap 23 is denoted as $g_2$, and the width of the third gap 24 is denoted as $g_3$.

In bipolar electrode arrangement, the width of the second gap $g_2$ be (approximately) 3 times the width of the first gap $g_1$.

The width of the third gap $g_3$ may be larger than the second gap $g_2$. For instance, the width of the third gap $g_3$ may be greater than twice as large at the width of the second electrode. In a specific example, the width of the third gap $g_3$ is equal to the sum of the widths of the first gap, the first electrode, the second gap and the second electrode. A larger third gap $g_3$ in comparison to the second gap $g_2$ (i.e. a smaller insulation portion at the first end 17 of the cuff relative to a larger insulation portion at the second end 18 of the cuff) assists in avoiding virtual cathodes.

For example, the width of the third gap $g_3$ may be 2.1 mm and the width of the second gap $g_2$ may be 0.9 mm. Thus, the width of the third gap $g_3$ may be greater than 1.8 mm. In a specific example, the width of the first gap is 0.3 mm, the width of second gap is 0.9 mm, the width of the third gap is 2.1 mm and the width of the first electrode is 0.3 mm, and when the width of the second electrode is 0.9 mm, and the width of the cuff is 4.5 mm.

Figure 6:
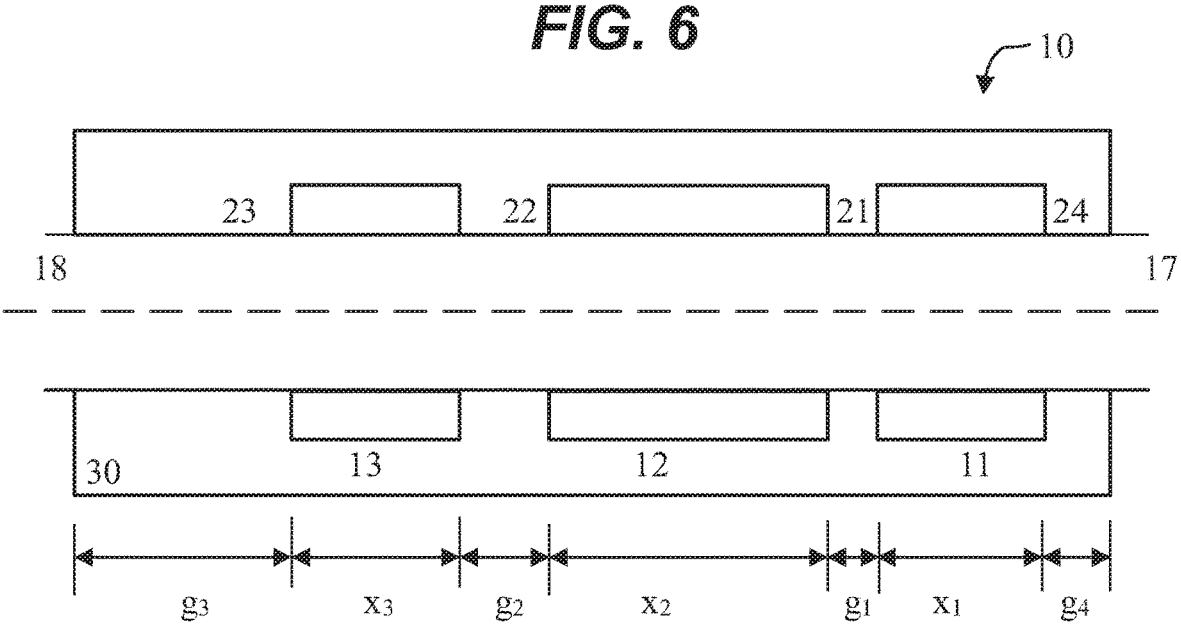
FIG. 6 illustrates a neural interface device with three electrodes and a flexible non-conductive layer.

Neural Interface Device (FIGS. 4 to 6)

A neural interface device 10 according to the disclosure is a device that is in physical contact with a nerve, where the nerve comprises a plurality of A-type nerve fibers. When an electrical signal is applied to the nerve via the neural interface device 10, the neural interface device 10 causes unidirectional stimulation of neural activity in the nerve, such as the vagus nerve in a human or an animal subject.

With reference to FIG. 4, the neural interface device 10 comprises an electrode arrangement 15. The electrode arrangement 15 is configured to be placed on or around the nerve when the neural interface device 10 is in use. The electrode arrangement 15 includes a plurality of electrodes 11, 12, 13 which are spaced apart from each other so as to define a gap between each of the electrodes, where each gap is positioned along the longitudinal axis of the nerve (i.e. in the direction of the longitudinal axis of the nerve). In particular, the electrode arrangement 15 of FIG. 4 and FIG. 5 includes a first electrode 11 and a second electrode 12 separated by a first gap ($g_1$) 21. The electrode arrangement 15 further includes a third electrode 13 that is separated from the second electrode 12 by a second gap ($g_2$) 22. This electrode arrangement is referred to as a tripolar electrode arrangement.

The first electrode 11, the second electrode 12 and the third electrode 13 can be cuff type electrodes (for example, spiral cuff, helical cuff or flat interface) which at least partially circumvent the nerve. For example, the first electrode 11, the second electrode 12 and the third electrode 13 shown in FIG. 4 are flat interface cuff electrodes which fully circumvent the nerve. However, other types of electrodes known in the art are also suitable for use in the electrode arrangement 15. For instances, one or more of flat interface electrodes, mesh electrodes, linear rod-shaped lead electrodes, paddle-style lead electrodes, disc contact electrodes, hook electrodes, sling electrodes, intrafascicular electrode, glass suction electrodes, paddle electrodes, and percutaneous cylindrical electrodes may be used.

The first electrode 11, the second electrode 12, and the third electrode 13 may fabricated from, or be partially or entirely coated with, a high charge capacity material such as platinum black, iridium oxide, titanium nitride, tantalum, poly(elthylene-dioxythiophene) and suitable combinations thereof, such as platinum-iridium alloy.

The surface area of each of the first electrode 11, the second electrode 12 and the third electrode 13 which is in contact with the nerve is specially adapted for unidirectional stimulation. In particular, the first electrode 11 has a first surface area and the second electrode 12 has a second surface area. The third electrode 13 has a third surface area.

In examples described herein, the surface area of the second electrode 12 may be larger than the surface area of the first electrode 11 and the surface area of the third electrode 13 respectively. In another example, the first gap ($g_1$) 21 between the first electrode 11 and the second electrode 12 may be different to (i.e. smaller or larger than) the second gap ($g_2$) 22 between the second electrode 12 and the third electrode 13. However, the first gap ($g_1$) 21 between the first electrode 11 and the second electrode 12 may be the same as the second gap ($g_2$) 22 between the second electrode 12 and the third electrode 13. In another example, the second surface area may be larger than the first surface area and the third surface area, and also the first gap ($g_1$) 21 between the first electrode 11 and the second electrode 12 may be different to (i.e. smaller or larger than) the second gap ($g_2$) 22 between the second electrode 12 and the third electrode 13.

In one example the device is operably connected to two stimulation devices. In this example, one stimulation device is connected to the first electrode 11 and the second electrode 12, and the other stimulation device is connected to the third electrode 13 and the second electrode 12. The stimulation devices can be operated to cause a different anodal charge to be injected at the first electrode 11 compared with the third electrode 13. In this example, where there are two stimulators the first gap ($g_1$) 21 between the first electrode 11 and the second electrode 12 may be different to (i.e. smaller or larger than) the second gap ($g_2$) 22 between the second electrode 12 and the third electrode 13 and/or the second surface area may be larger than the first surface area and the third surface area. However, the first gap ($g_1$) 21 between the first electrode 11 and the second electrode 12 may be the same as the second gap ($g_2$) 22 between the second electrode 12 and the third electrode 13.

In an electrode arrangement 15 which uses cuff type electrodes that fully circumvent the nerve, the size of this surface area can be calculated by multiplying 7C (i.e. 3.14159) by the internal diameter and width of the respective electrode (i.e. the first electrode 11, the second electrode 12 or the third electrode 13). Since the internal diameter of the first electrode 11, the second electrode 12 and the third electrode 13 is fixed by the diameter of the nerve, the surface area of each of the first electrode 11, the second electrode 12 and the third electrode 13 in contact with the nerve is adjusted by changing the width of the electrode. In one example, the internal diameter of the first, second and third electrodes may be 0.5 mm.

The width of each of the first electrode 11, the second electrode 12 and the third electrode 13 is defined as the distance the electrode spans along the longitudinal axis of the nerve. In FIG. 5, the width of the first electrode 11 is denoted $x_1$, whilst the width of the second electrode is denoted $x_2$ and the width of the third electrode is denoted $x_3$.

The width of the first electrode $x_1$ is defined by the user. Typically, the width of the first electrode $x_1$ is around 0.3 mm. The width of the third electrode $x_3$ may also be user defined and typically around 0.3 mm.

Similarly, the width of the first gap between the first electrode 11 and the second electrode 12 is defined as the distance that the gap spans along the longitudinal axis of the nerve. In FIG. 5, the width of the first gap is denoted $g_1$. The width of the second gap between the second electrode 11 and the third electrode 13 is defined as the distance that the gap spans along the longitudinal axis of the nerve. In FIG. 5, the width of the second gap is denoted $g_2$.

The width of the first gap $g_1$ is also defined by the user. Typically, the width of the first electrode $x_1$ is around the same size as the first gap $g_1$, which in this example is 0.3 mm. The width of the second gap $g_2$ is also defined by the user. In one example, the width of the second gap $g_2$ is at least or greater than the sum of the width of the second electrode and the first gap $g_1$. For instance, the width of the second gap may be 6 mm.

The surface area of the second electrode 12 is adapted to be larger than the surface area of the first electrode 11 and the third electrode 13. When the surface area of the second electrode 12 is larger than the surface area of the first electrode 11 this concentrates charge density under the first electrode 11 for a given current compared to charge under the second electrode 12, thus strengthening the hyperpolarization of the nerve without increased energy requirements. Thus, the width of the second electrode $x_2$ may be greater than the width of the first electrode $x_1$ and the third electrode $x_3$ respectively.

The width of the second electrode $x_2$ may be the sum of the width of the first electrode (i.e. the first width) and the width of the third electrode (i.e. the third width). In another example, the width of the second electrode (i.e. the second width) may be two times the first electrode width or the third electrode width.

For example, the width of the second electrode $x_2$ may be at least two, three, four or five times the width of the first electrode $x_1$ and the third electrode $x_3$ respectively.

Where two stimulators are used to provide a different anodal charge density at the first electrode in comparison to the charge at the third electrode, the asymmetry in the charge provided by the first and third electrodes allows directional stimulation to occur, without the need for different surface areas at the electrodes or different spacing between the electrodes to be provided. However, these features may be provided to enhance the directionality of the stimulation.

In the electrode arrangement, the width of the second electrode $x_2$ may also be less than or equal to five times the width of the first electrode $x_1$ and the third electrode $x_3$ respectively. This is to reduce the separation between activation threshold under the second electrode 12 and blocking threshold under the first electrode 11.

For example, the width of the second electrode $x_2$ may be one of: $2.0x_1$, $2.5x_1$, $3.0 x_1$, $3.5x_1$ $4.0 x_1$, $4.5x_1$, $5.0 x_1$, $5.5x_1$, $6.0 x_1$, $6.5x_1$, $7.0 x_1$, $7.5x_1$, $8.0 x_1$, $8.5x_1$, $9.0 x_1$, $9.5x_1$ or $10.0x_1$. In other words, the ratio of the surface area of the second electrode to the ratio of the surface area of the first electrode may be 2 (2:1), 2.5 (5:2), 3 (3:1), 3.5 (7:2), 4 (8:2), 4.5 (9:2), 5 (5:1), 5.5 (11:2), 6 (6:1), 6.5 (13:2), 7 (14:1), 7.5 (15:2), 8 (8:1), 8.5 (17:1), 9 (9:1), 9.5 (19:2), or 10 (10:1).

For example, the width of the second electrode $x_2$ may be one of: $2.0x_3$, $2.5\ x_3$, $3.0\ x_3$, $3.5\ x_3$, $4.0x_3$, $4.5\ x_3$, $5.0x_3$, $5.5\ x_3$, $6.0x_3$, $6.5\ x_3$, $7.0x_3$, $7.5\ x_3$, $8.0x_3$, $8.5\ x_3$, $9.0x_3$, $9.5\ x_3$ or $10.0x_3$. In other words, the ratio of the surface area of the second electrode to the ratio of the surface area of the first electrode may be 2 (2:1), 2.5 (5:2), 3 (3:1), 3.5 (7:2), 4 (8:2), 4.5 (9:2), 5 (5:1), 5.5 (11:2), 6 (6:1), 6.5 (13:2), 7 (14:1), 7.5 (15:2), 8 (8:1), 8.5 (17:1), 9 (9:1), 9.5 (19:2), or 10 (10:1).

To achieve unidirectional stimulation, the first electrode 11 and the third electrode 13 are both positively charged electrodes, and the second electrode 12 is a negatively charged electrode, also referred to as the "cathode".

The width (or surface area) of the first electrode relative to the width (or surface area) of the second electrode has been found to allow the device to provide an efficacious signal, while reducing the magnitude of the current required. This advantage is explained in greater detail in the summary above.

The neural interface device 10 may further comprise a flexible non-conductive layer 30, as shown in FIG. 6. In other words, the flexible non-conductive layer 30 is an insulator. The electrode arrangement 15 may be mounted on to or otherwise attached to the flexible non-conductive layer 30. When in use, the electrode arrangement 15 interfaces the nerve and the flexible non-conductive layer interfaces the electrode arrangement 15. The flexible non-conductive layer 30 may conform to the shape of the electrodes such that it resides in the first gap 21 between the first and second electrodes 11, 12 and additionally interfaces the nerve in that gap. The flexible non-conductive layer 30 may reside in a second gap 22 between the second electrode 12 and the third electrode 13. The flexible non-conductive layer 30 may reside in a third gap ($g_3$) 23 between the third electrode 13 and a second end 18 of the device 10. The flexible non-conductive layer 30 may reside in a fourth gap ($g_4$) 24 between a first end 17 of the device 10 and the first electrode.

The flexible non-conductive layer 30 may be made from a polysiloxanes (i.e. silicone) or a similar material to allow the flexible non-conductive layer to conform to the shape of the nerve. In some embodiments, the flexible non-conductive 30 layer is configured to at least partially circumvent the nerve when in use. The flexible non-conductive layer 30 may fully circumvent the nerve, as shown in FIG. 6.

The flexible non-conductive layer may form a cuff around the nerve. The cuff may be fastened in place on the nerve using any means known in the art. The cuff has two open ends which are perpendicular to the longitudinal axis of the nerve. The first open end 17 and second open end 18 of the cuff are shown in FIG. 6.

A second gap 22 is defined as the gap along the longitudinal axis of the nerve between the second electrode 12 and the third electrode. The second gap 23 defines a first non-conductive portion.

Similarly, a third gap 23 is defined as the gap along the longitudinal axis of the nerve between the second open end 18 and the third electrode 13 in a bipolar electrode arrangement (shown in FIG. 6). The third gap 23 defines another non-conductive portion. As shown in FIG. 6, the width of the second gap 22 is denoted as $g_2$, and the width of the third gap 23 is denoted as $g_3$.

The width of the third gap 23 $g_3$ may be larger than the second gap 22 $g_2$. For instance, the width of the third 23 gap $g_3$ may be greater than twice as large at the width of the second electrode 12.

In the above-mentioned example, the first gap is different to the second gap, and thus provides an asymmetrical configuration that allows unidirectional stimulation to be achieved. For instance, the first gap may be larger than the second gap, or the second gap may be larger than the first gap. In another example, the first electrode 11 is arranged to provide a different charge to the charge arranged to be provided by the third electrode 13, which provides asymmetric electrode configuration in this example.

Referring to FIGS. 4 to 6, the configuration for the creation of unidirectional action potentials in the nerve is a tripolar 'passive imbalance' configuration. The second electrode 12 is positioned along the nerve axis proximal to the first electrode 11 and the third electrode 13 is positioned along the nerve axis proximal to the second electrode 12.

The electrode configuration may employ asymmetric spatial variance to provide a passive imbalance such that the first gap 21 $g_1$ between the first electrode 11 and the second electrode 12 is shorter than the second gap 22 $g_2$ between the second electrode and the third electrode 13. In this configuration, when an electrical signal is applied to the first electrode 11 and the third electrode 13 such that they become positively charged (anode) and an electrical signal is applied to the second electrode 12 such that it becomes negatively charged (cathode), and when the pulse width of the electrical signals applied is tuned with the inter-electrode distance for fiber type conduction velocities, there is an impedance mismatch conveyed by the current path length along the nerve. The first electrode 11 has a larger current density than the third electrode 13. The neural interface devices may comprise a dual current source and tri-polar electrode arrangements with different insulation spacing.

In this example, the second gap $g_2$ may be specially adapted for unidirectional stimulation. A compound action potential is impeded under the first electrode 11 by adapting the pulse width of the electrical signal applied to the nerve based the width of the first gap 21 $g_1$. This is so that the compound action potential generated under the second electrode 12 arrives in the nerve under the first electrode 11 when hyperpolarization of the nerve is present. In order for the compound action potential travelling in the opposite direction along the nerve not to be impeded under the third electrode 13, the nerve under the third electrode 13 should not be hyperpolarized when the compound action potential arrives. In some embodiments, the neural activity of the nerve under the third electrode 13 has returned to baseline activity upon arrival of the compound action potential, allowing the compound action potential to pass unimpeded. This can be achieved by adapting the width of the second 22 gap $g_1$ based on the width of the first 21 gap $g_1$.

The width of the second 22 gap $g_2$ may be greater than the sum of the width of the first gap 21 $g_1$ and the width of the second electrode 12.

Another exemplary electrode configuration for creation of unidirectional action potentials in a nerve is a tri-polar 'active, current balance' configuration comprising a first electrode 11, a second electrode 12 and a third electrode 13. The second electrode 12 is positioned along the nerve axis proximal to the first electrode 11 and the third electrode 13 is positioned along the nerve axis proximal to the second electrode 12, where the spacing between the first electrode 11 and the second electrode 12 is the same distance as the spacing between the second electrode 12 and the third electrode 13. Additionally, the surface area of the first electrode 11 in contact with the nerve is equal in size to the surface area of the second electrode 12 in contact with the nerve, and to the surface area of the third electrode 13 in contact with the nerve. Two independent non-equal current sources in the implantable pulse generator (IPG) provide positive currents to the first electrode and the third electrode respectively and the second electrode shares or sums the negative lead from both current sources. In this configuration, the current source of the first electrode 11 provides a greater current than the current source of the third electrode 13 such that the third electrode 13 becomes more positively charged (anode) than the first electrode 11. The second electrode 12, which shares both current sources, becomes negatively charged (cathode). The current density mismatch between the first and third electrodes steers action potentials in the direction away from the first electrode 11.

Neural interfaces may comprise a dual current source and tri-polar electrode arrangements with different insulation spacing.

The surface area of the second electrode 12 can be adapted to be larger than the surface area of the first electrode 11 so that charge density is concentrated under the first electrode 11, thus strengthening the hyperpolarization of the nerve without increased energy requirements. Thus, the width of the second electrode 12 $x_2$ (in the longitudinal direction) is greater than the width of the first electrode 11 $x_1$ (in the longitudinal direction). In particular, the width of the second electrode 12 $x_2$ can be at least twice the width of the first electrode 11 $x_1$. The second electrode 12 therefore has at least twice the surface area than the first electrode 11. In this example, reducing the surface area of the first electrode 11 relative to the second electrode 12 reduces the charge density over the second electrode 12 (i.e. the cathode).

In a tri-polar electrode arrangement, the width of the second electrode 12 $x_2$ may also be less than or equal to ten times the width of the first electrode 11 $x_1$.

Thus, in a tri-polar electrode arrangement, the width of the second electrode 11 $x_2$ may be set at any value between the upper and lower limits described above. For example, the width of the second electrode 12 $x_2$ may be one of: $2.0x_1$, $2.5x_1$, $3.0x_1$, $3.5x_1$, $4.0x_1$, $4.5x_1$, $5.0x_1$, $5.5x_1$, $6.0 x_1$, $6.5x_1$, $7.0 x_1$, $7.5x_1$, $8.0 x_1$, $8.5x_1$, $9.0 x_1$, $9.5x_1$ or $10.0x_1$. Typical values for the width of the first electrode $x_1$ are described above.

The width of the third electrode 13 $x_3$ may be at least the width of the first electrode 11 $x_1$.

Experimental Method

Naive male Hartley guinea pigs were euthanized via Intraperitoneal barbiturate injection (Fatal-Plus) according to IACUC approved protocols. Tissue was assayed and processed in Krebs-Henseleit buffer (mM): NaCl (113.0), KCl (4.8), $CaCl_2$ (2.5), $KH_2PO_4$ (1.2), $MgSO_4$ (1.2), $NaHCO_3$ (25.0), dextrose (5.55), equilibrated with 95% $O_2$: 5% $CO_2$.

Left or right vagi, spanning 40-60 mm from the nodose and jugular ganglia to the subclavian arteries with the carotid artery were removed for processing. Under dissection microscopes, the vagus was separated from the carotid artery, connective tissue, and fat and partially de-sheathed. Tissue was transferred and mounted to a custom 3 chamber tissue with surgical silk (5.0). All chambers were filled with fresh assay buffer perfused for 30-60 min at 35+/−2° C. prior to recording.

Stimulation was performed in the central chamber on the cervical vagus with custom made 500 μm platinum/iridium silicone cuff electrodes. Stimuli of varying pulse duration (PD) and current were generated with a square-pulse stimulator (Grass model S48; Natus Neurology Inc., Warwick, R.I., U.S.A.) driving an optically isolated constant current source (Model 2200; AM Systems, Seqium, Wash., U.S.A.). Quasitrapezoidal pulses were generated by the addition of a schottky diode to a parallel resistor (770-5770 Ohm)/capacitor (0.1 uF) network prior to isolation. In some cases, the quasitrapezoidal stimulus was generated via a Kiethley 3390 50 MHz arbitrary waveform generator using KI Wave software v1.2 (Tektronix, Beaverton, Oreg., U.S.A) and fed into the constant current stimulus isolator.

Stimulation was applied centrally with compound action potentials recorded on the distal and proximal vagus with a microelectrode AC amplifier (A-M Systems model 1800, Carlsborg, Wash., U.S.A.) using Ag/AgCl hook electrodes in the outside baths. Arrest side of stimulus was always oriented proximally. Differential signals were filtered with a low cut-off frequency of 10 Hz and high cut-off frequency of 1 kHz. Tissue was grounded via a platinum hook electrode in the central bath. After checking viability of tissue, the recording baths were drained and rapidly filled with pre-warmed mineral oil and recording commenced.

Analog signals were digitized at 15 kHz using an analog-to-digital converter (Power1401 625 kHz;

Cambridge Electronic Design Ltd., Cambridge, England, UK) and Spike 2 software (v5.21, Cambridge Electronic Design Ltd). Non-linear regressions were performed in Graphpad Prism (v5.03, GraphPad Software, San Diego Calif. USA).

Results are normalized to the maximal area under a curve observed for given fiber type from a square pulse stimulation.

Figure 7:
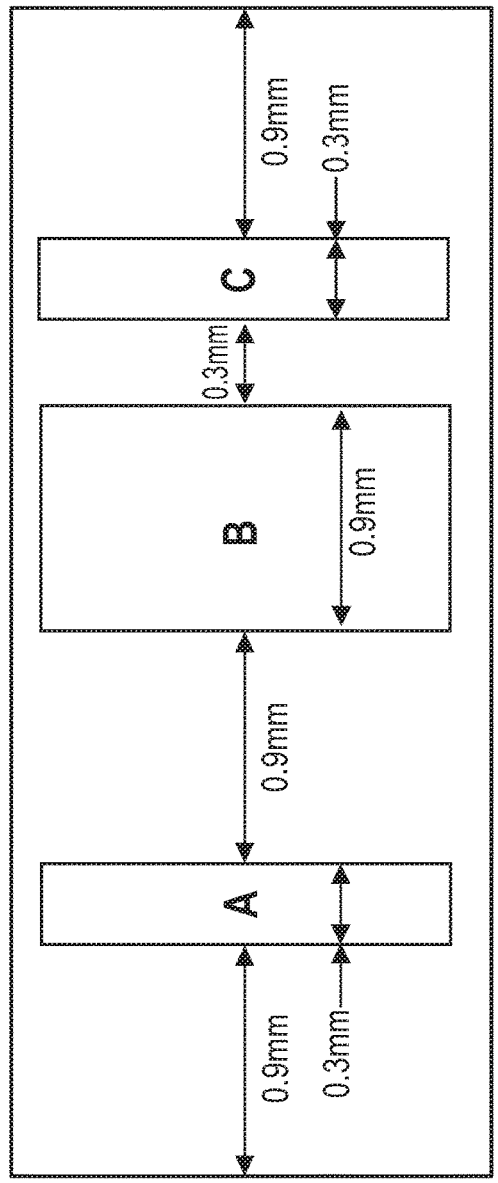
FIG. 7 illustrates an electrode configuration.

Cuff Design #1 (FIG. 7)

FIG. 7 illustrates an electrode configuration where electrodes A and C are anodes and electrode B is a cathode. The dimensions of the configuration are as follows (using the same notation as described with reference to FIG. 6):

| Parameter | Dimension (mm) |
| --- | --- |
| g3: | 0.9 |
| x3: | 0.3 |
| g2: | 0.9 |
| x2: | 0.9 |
| g1: | 0.3 |
| x1: | 0.3 |
| g4: | 0.9 |

In this configuration the first and the third electrode are equal in width and have the same surface area. The width of second electrode is three times that of the first or the third electrode. The gap between the third and the second electrode is three times that of the gap between the first and the second electrode.

Figure 8:
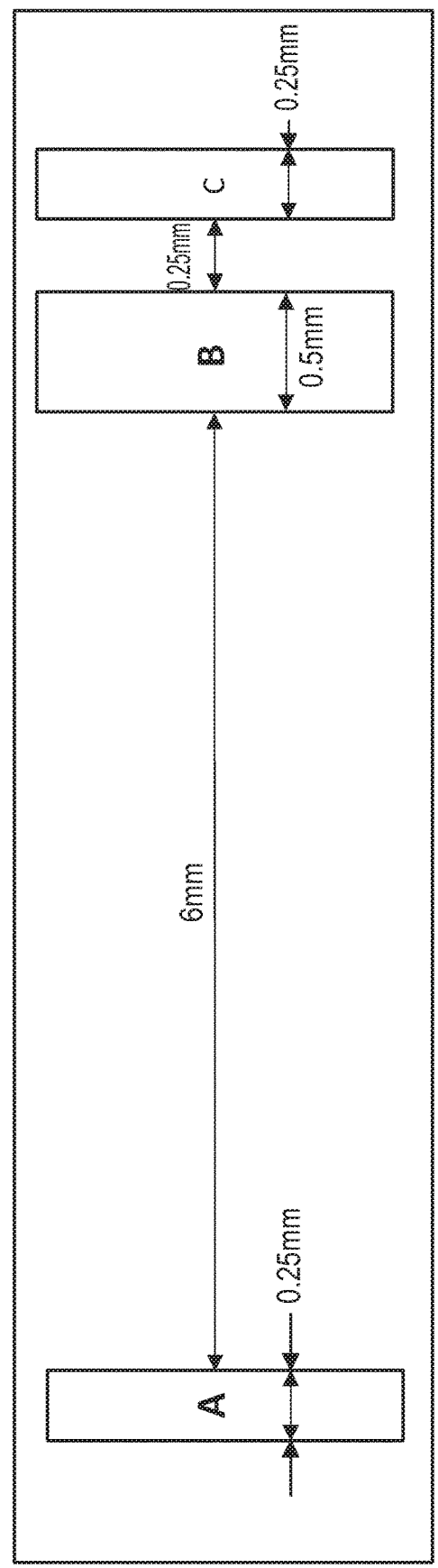
FIG. 8 illustrates another electrode configuration
Figure 9A:
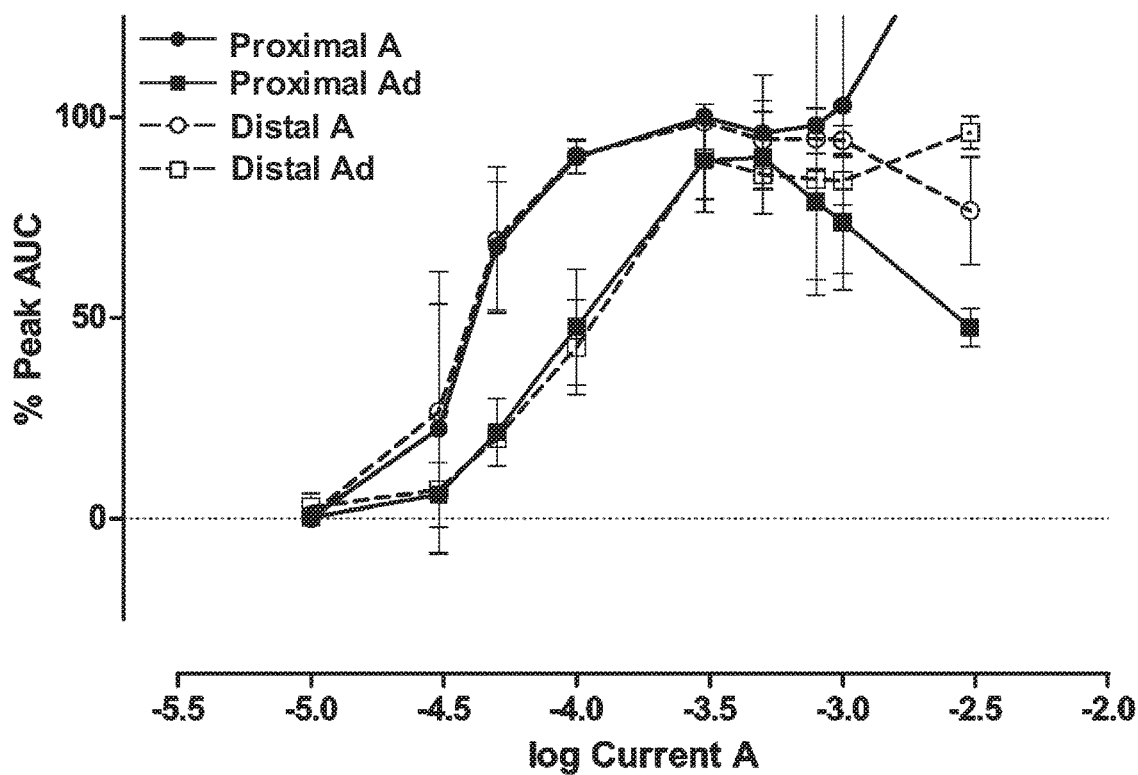
FIGS. 9A-D illustrate action potential propagation distal and proximal to a central electrode array when the electrode configuration of FIG. 7 is stimulated in a bipolar manner with a square pulse.
Figure 9B:
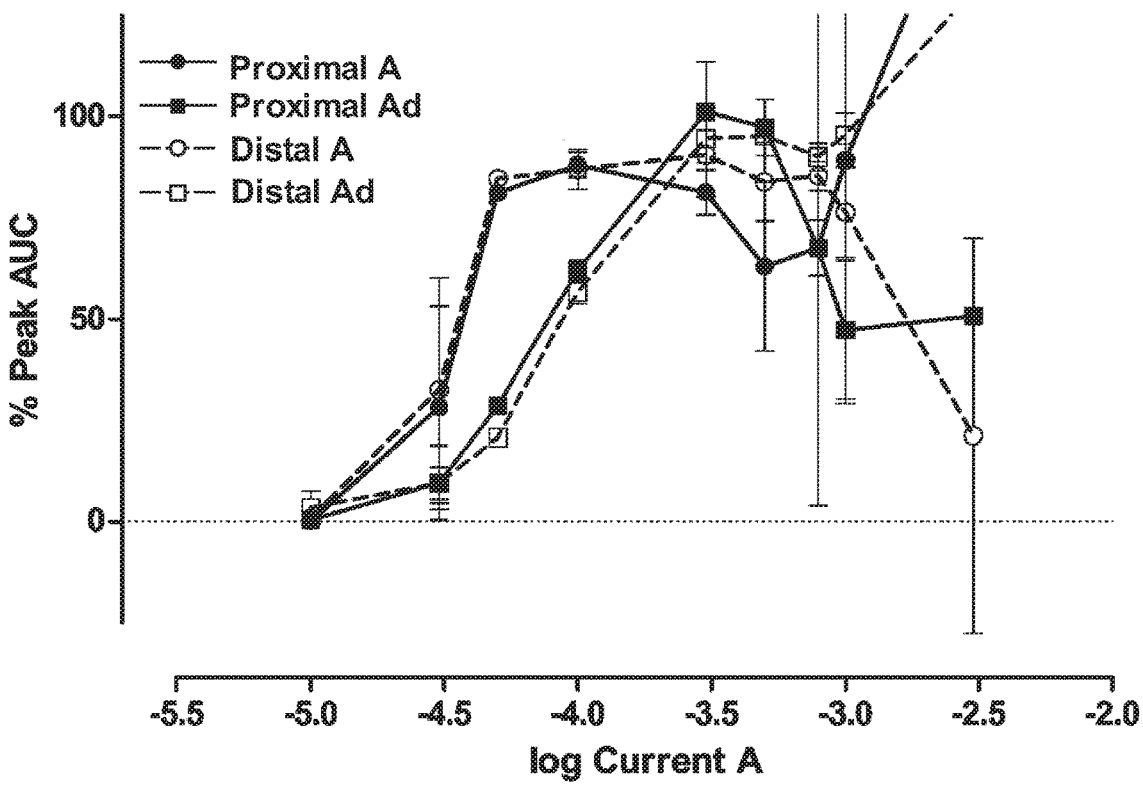
Figure 9C:
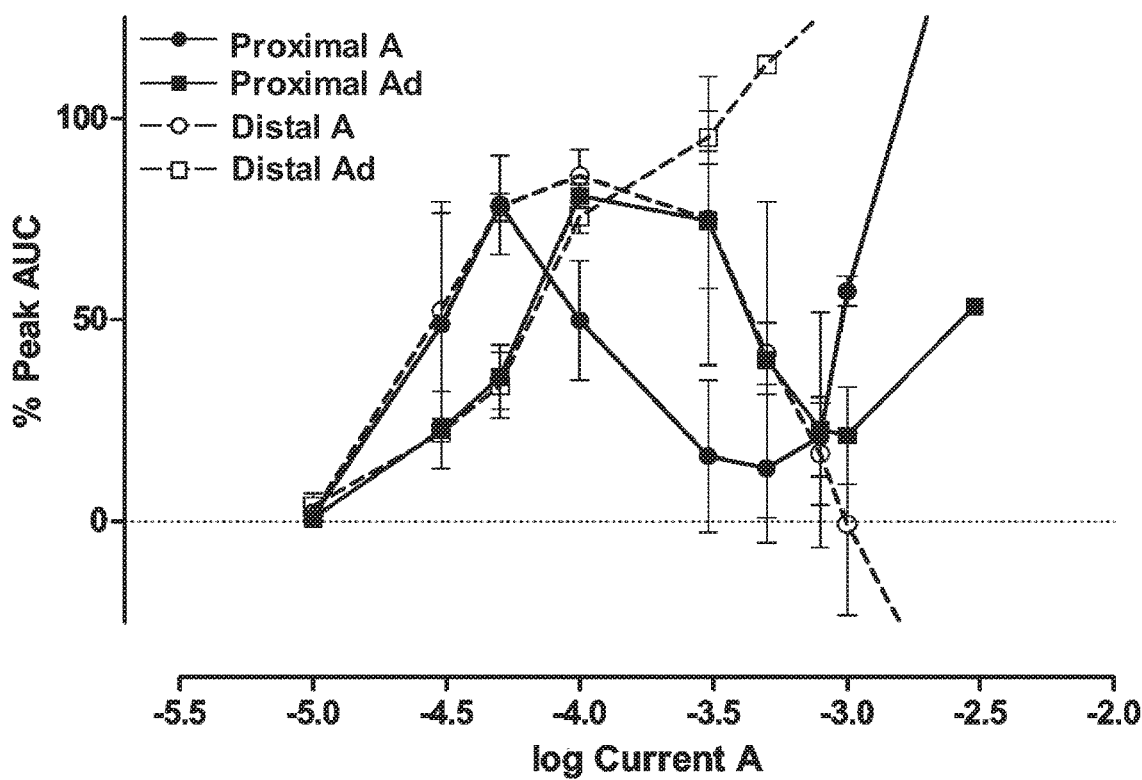
Figure 9D:
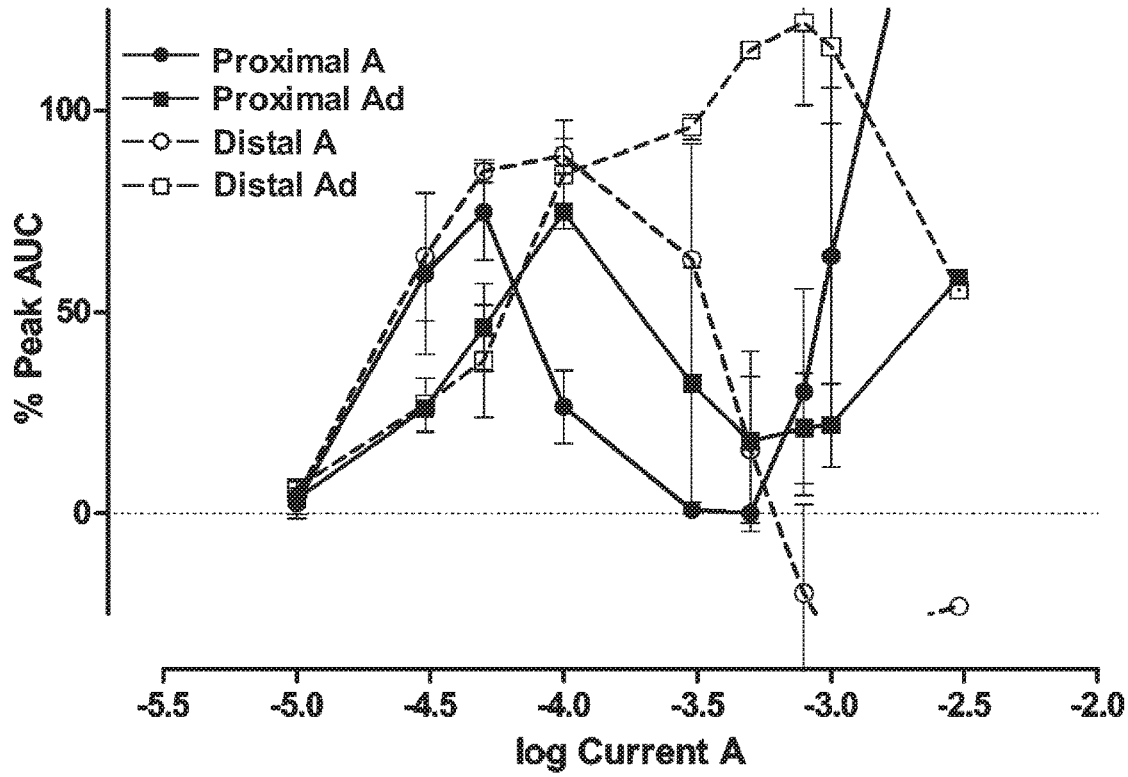
Figure 10C:
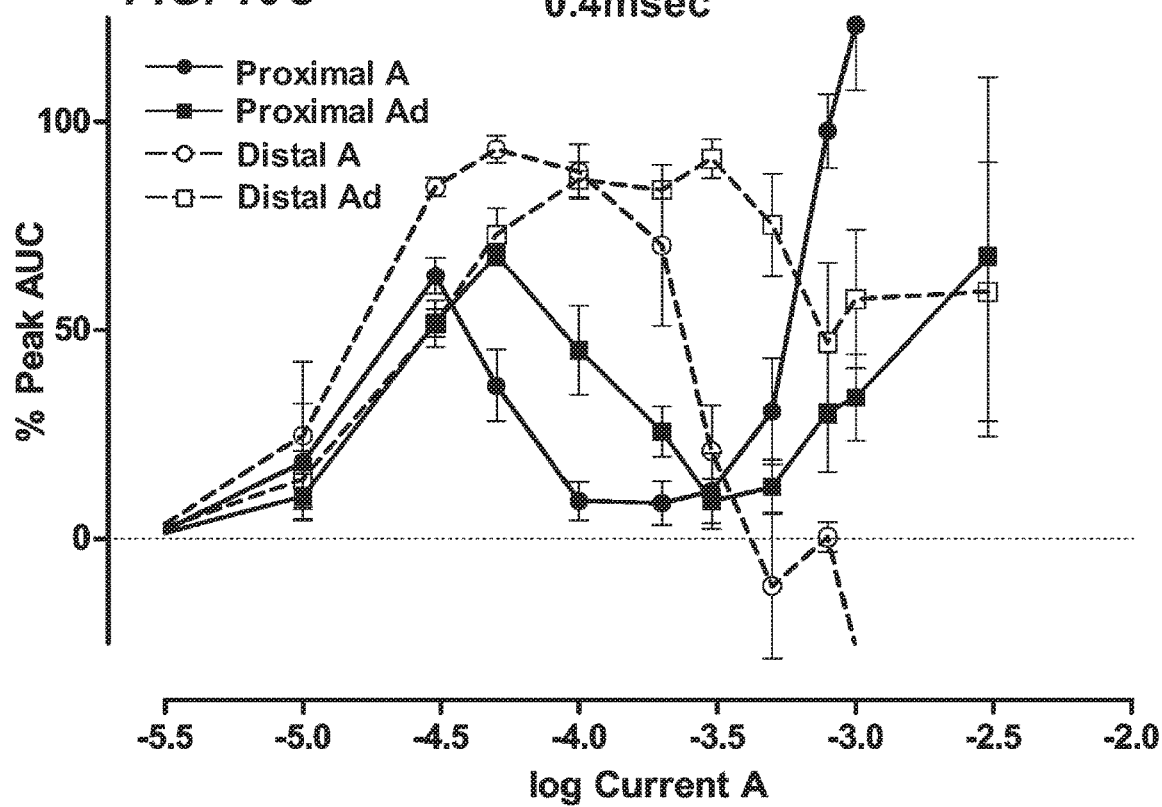
Figure 10D:
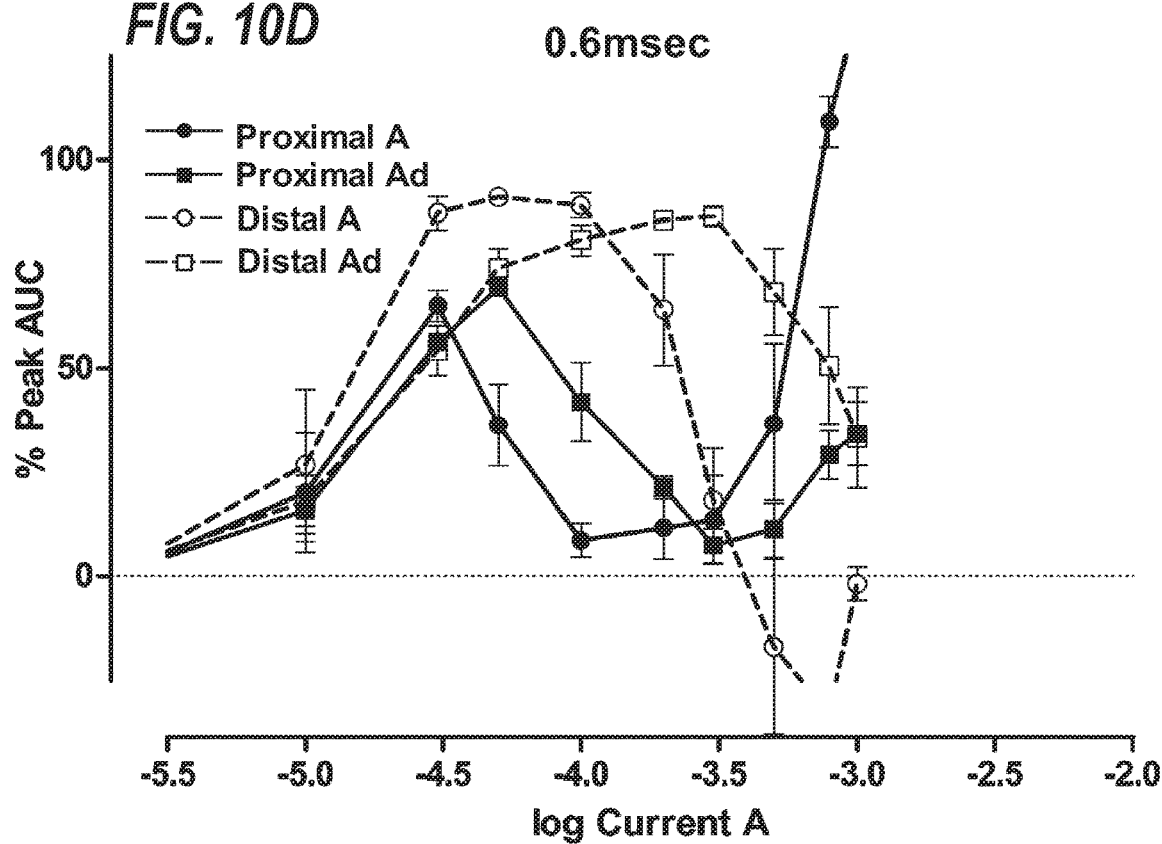
Figure 11A:
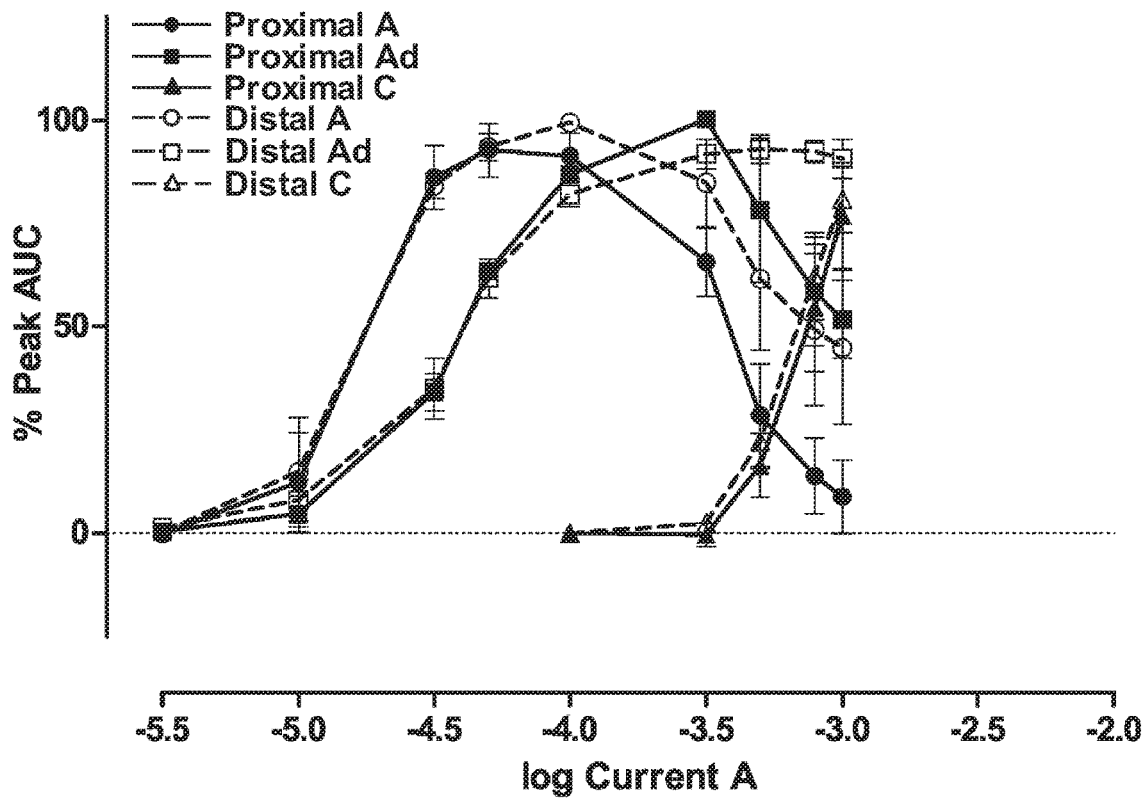
FIGS. 11A-D illustrate action potential propagation distal and proximal to a central electrode array when the electrode configuration of FIG. 7 is stimulated in a tripolar manner with a quasitrapezoidal pulse.
Figure 11B:
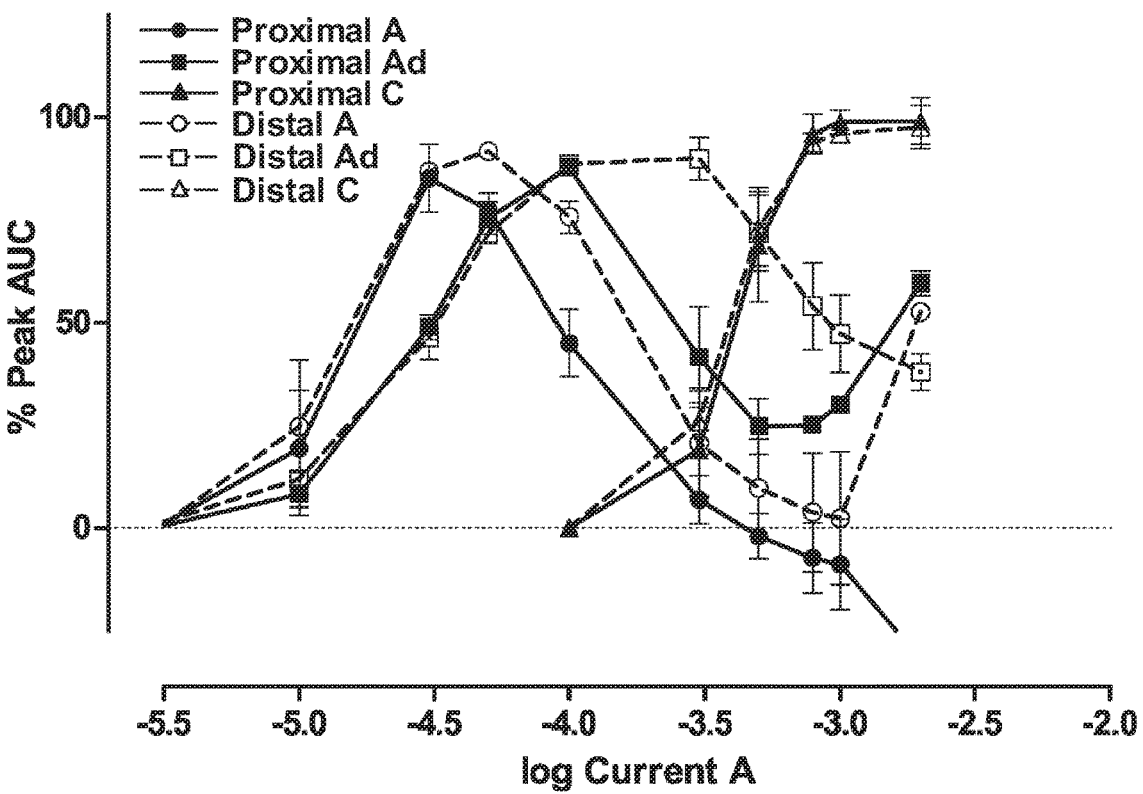
Figure 11C:
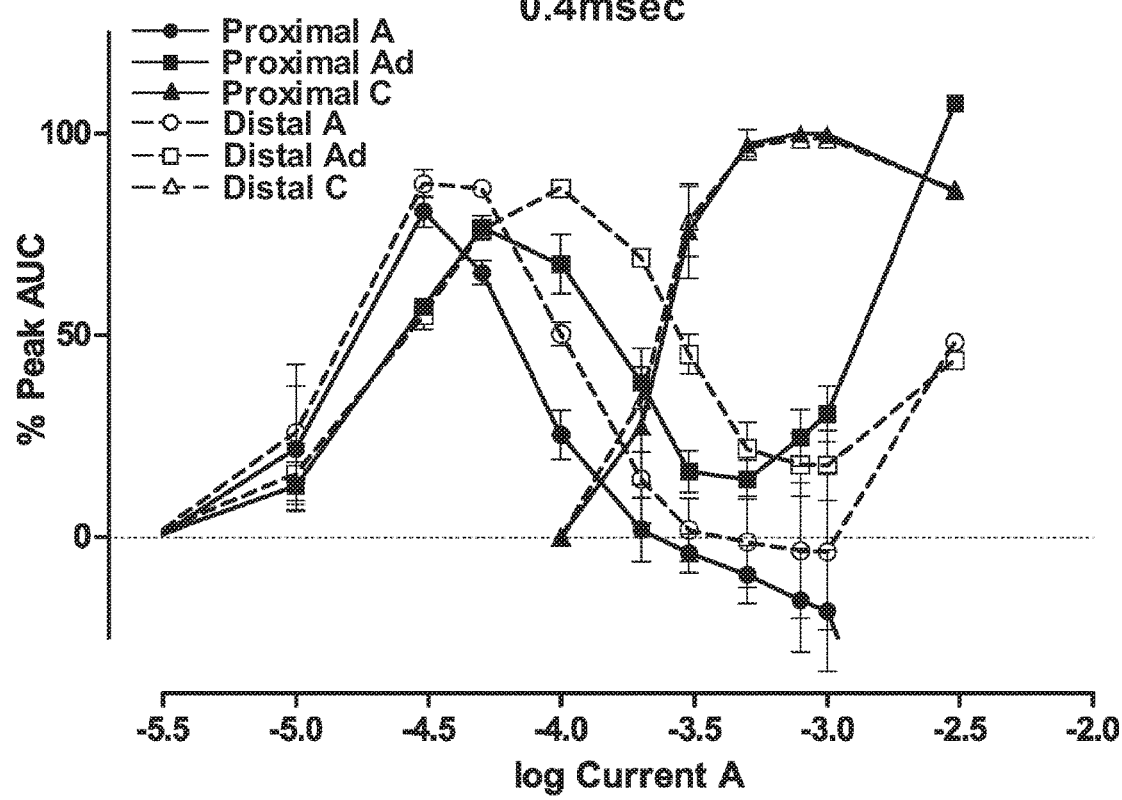
Figure 11D:
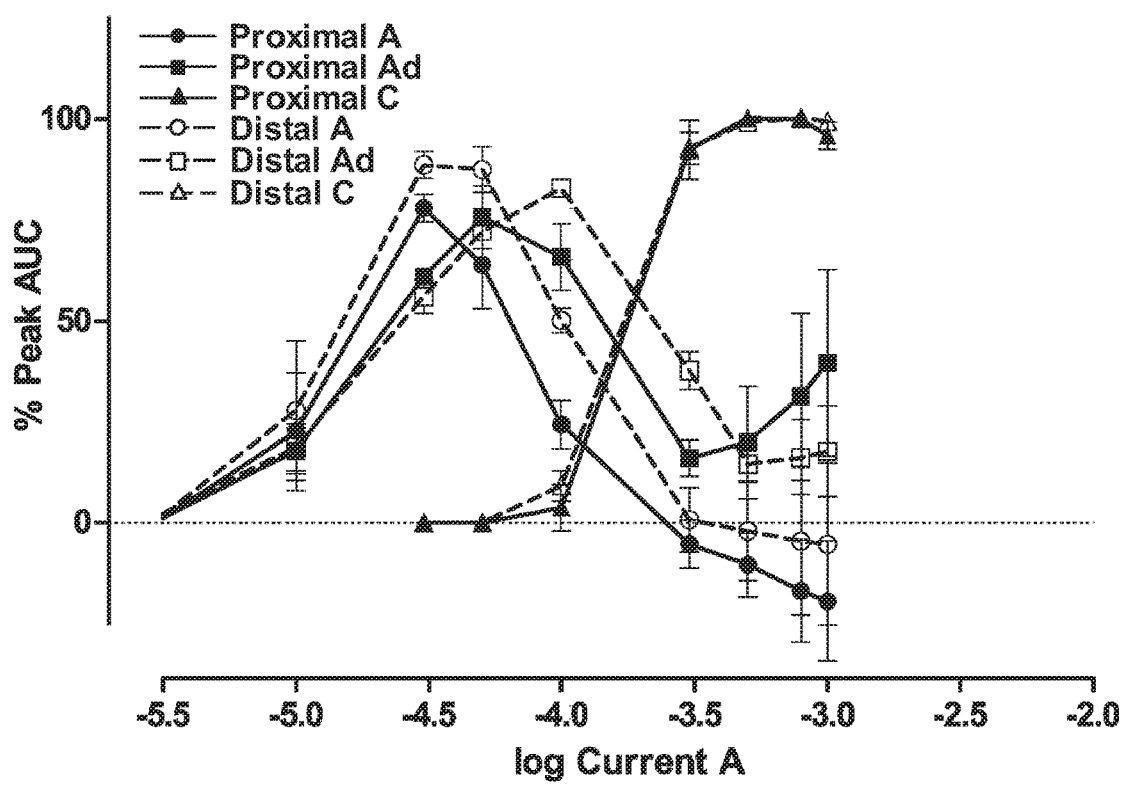
Figure 12A:
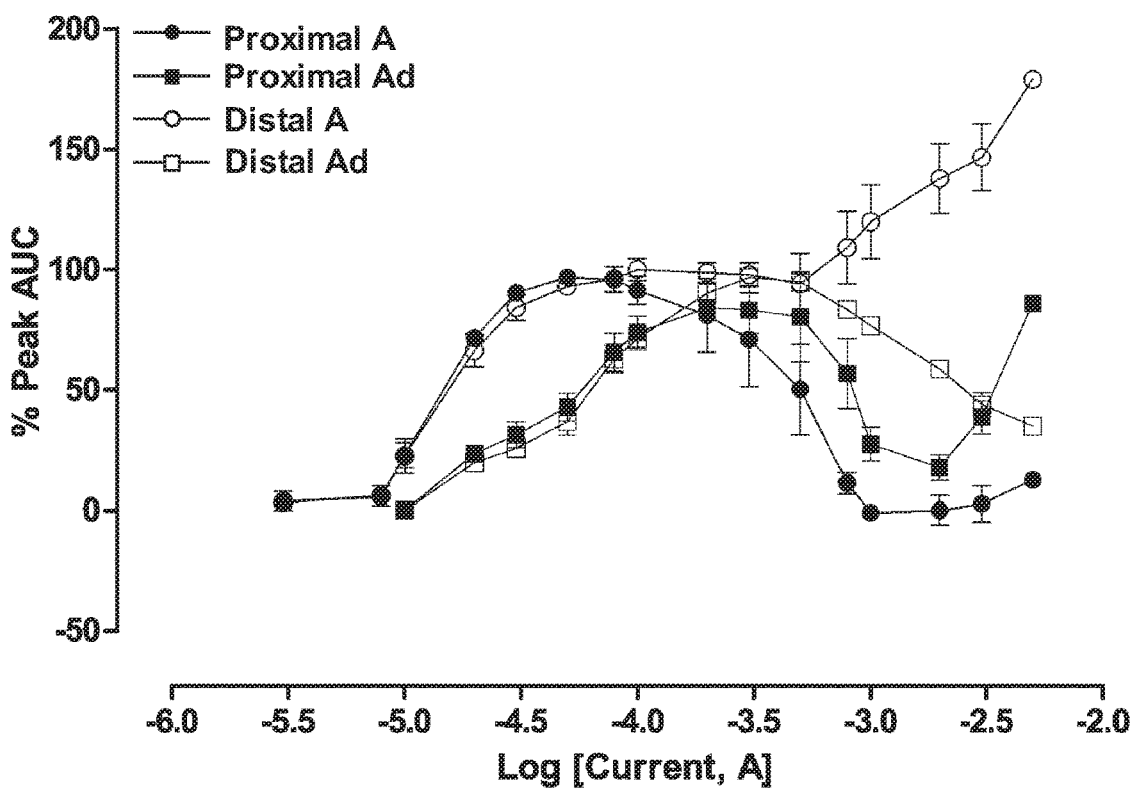
FIGS. 12A-D illustrate action potential propagation distal and proximal to a central electrode array when the electrode configuration of FIG. 8 is stimulated in a tripolar manner with a quasitrapezoidal pulse.
Figure 12B:
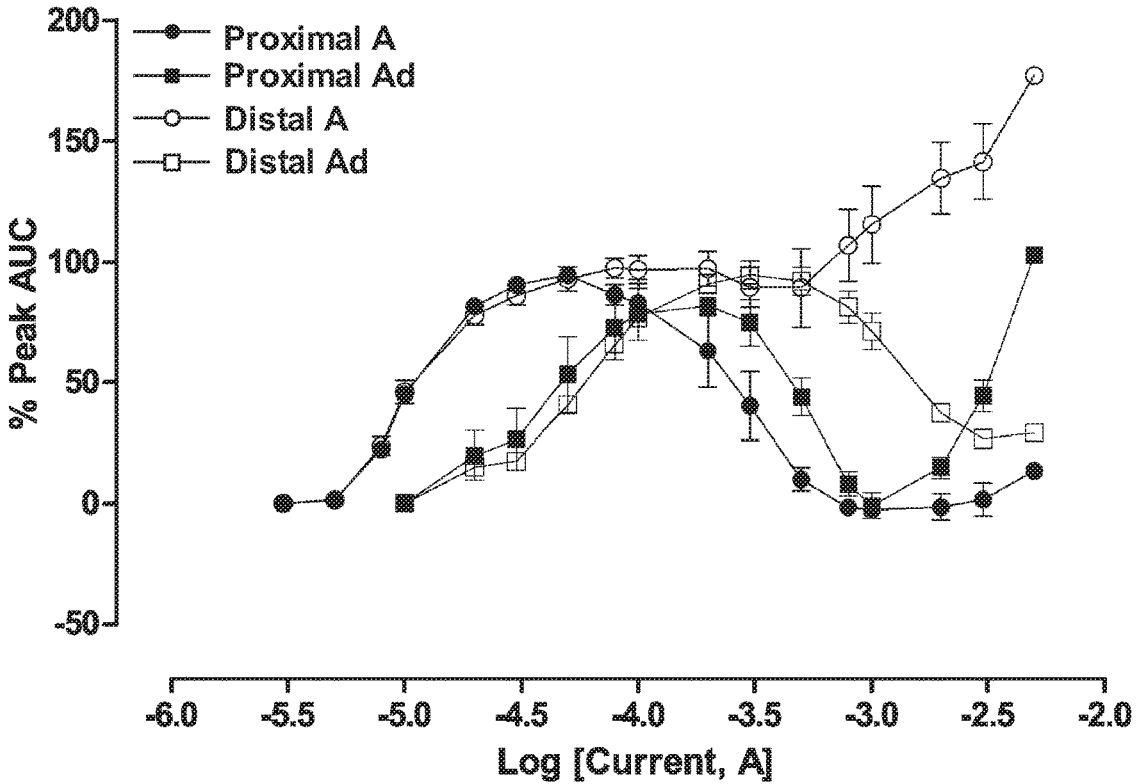
Figure 12C:
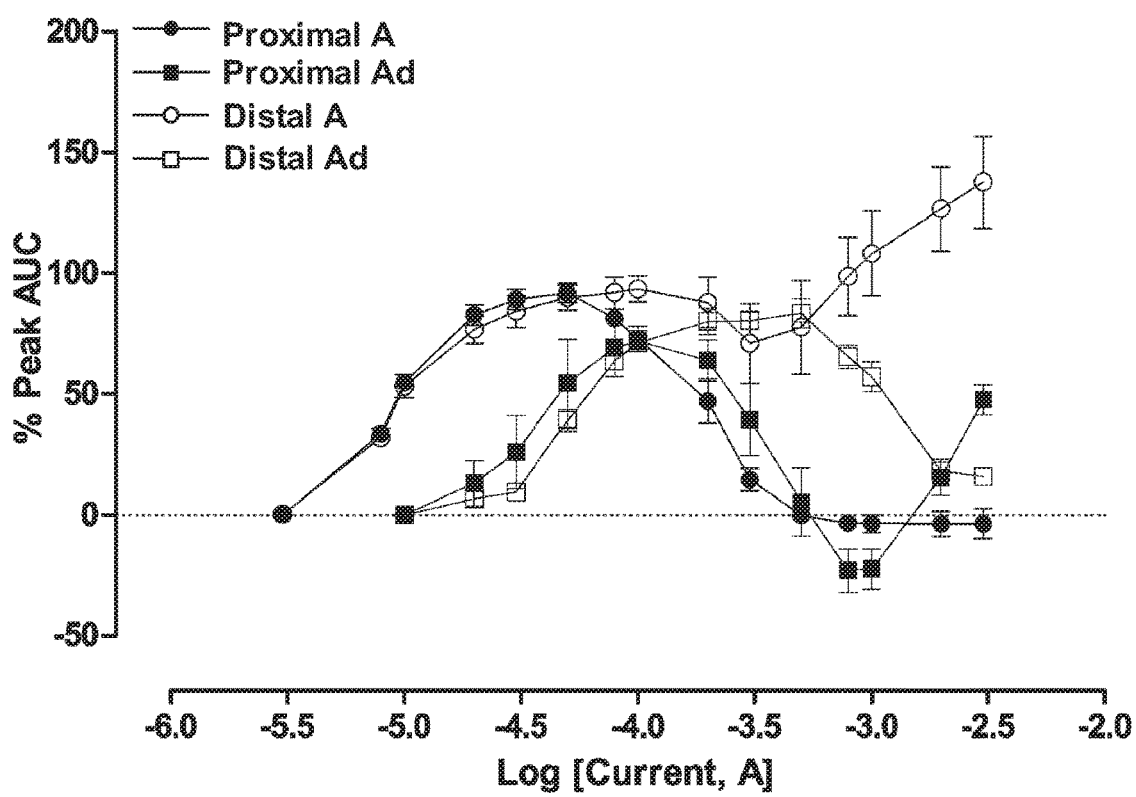
Figure 12D:
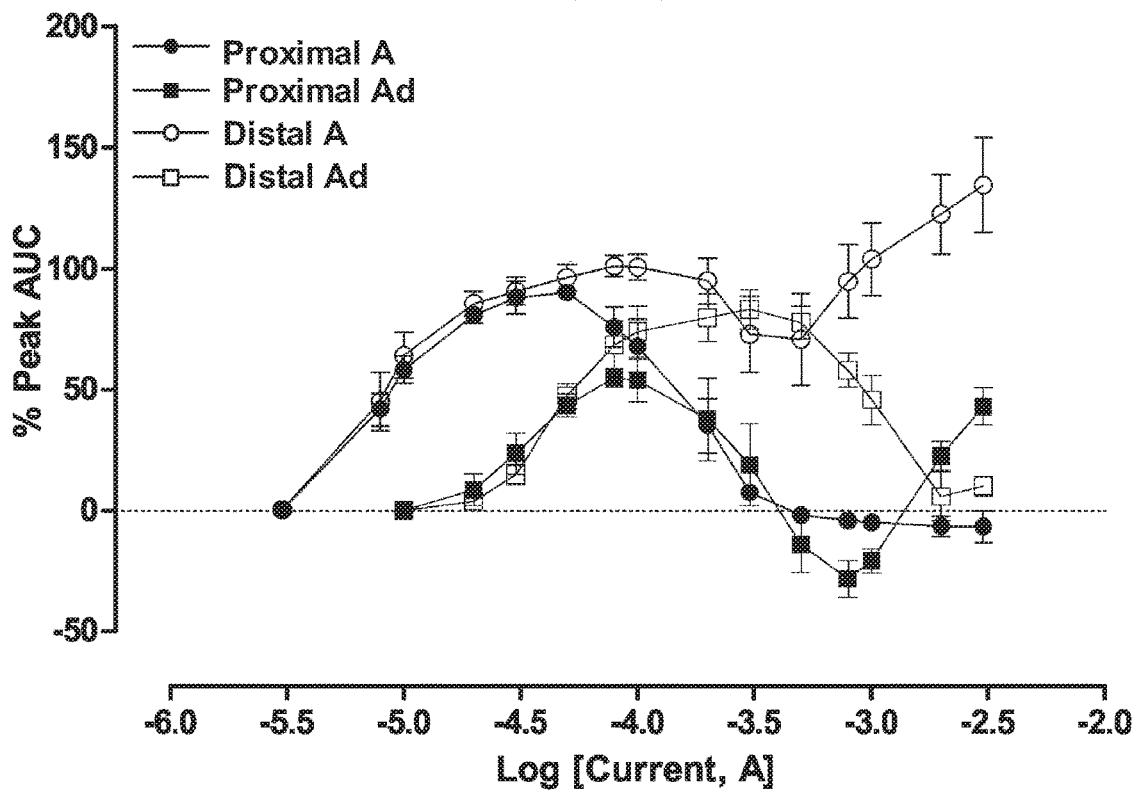

Cuff Design #2 (FIG. 8)

FIG. 8 illustrates an electrode configuration where electrodes A and C are anodes and electrode B is a cathode. The dimensions of the configuration are as follows (using the same notation as described with reference to FIG. 6):

| Parameter | Dimension (mm) |
| --- | --- |
| $x_3$: | 0.25 |
| $g_2$: | 6.0 |
| $x_2$: | 0.5 |
| $g_1$: | 0.25 |
| $x_1$: | 0.25 |

In this configuration the first and the third electrode are equal in width and have the same surface area. The width of second electrode is two times that of the first or the third electrode. The gap between the third and the second electrode is twenty-four times that of the gap between the first and the second electrode.

Experimental Results (FIGS. 9A-D)

FIGS. 9A-D illustrate the results of bipolar square pulse stimulation (0.1-0.6 msec, monophasic) of a guinea pig vagus using cuff design #1 where the cathode (electrode B) is three times the geometric surface area of the anode (electrode C). The pulse durations (0.1-0.6 msec) refer to the duration of the pulse where the peak amplitude is provided (i.e. the plateau of the square wave). The stimulation was provided with one current source attached to the cathode and an anode (i.e. 'passive stimulation' was provided).

The A fibers (having a conduction velocity of ~>10 m/s) are donated by the red circles. The Ad fibers (having a conduction velocity of ~10-3 m/s) are denoted by the blue squares. A pulse width (plateau phase) dependent suppression of compound action potential propagation can be observed in the proximal direction (solid symbols) for both A and Ad fiber types, with a preference for propagation distally (open symbols). A virtual cathode/anode formation occurs close to 1 mA.

Experimental Results (FIGS. 10A-D)

FIGS. 10A-D illustrate the results of bipolar quasitrapezoidal stimulation (0.1-0.6 msec plateau phase, >200 us decay) of guinea pig vagus using cuff design #1 where the cathode (electrode B) is 3× the geometric surface area of the anode (electrode C). The pulse durations (0.1-0.6 msec) refer to the duration of the pulse where the peak amplitude is provided (i.e. the plateau of the quasitrapezoidal wave before the amplitude begins to decay). The stimulation was provided with one current source attached to the cathode and an anode (i.e. 'passive control' was provided).

The A fibers (having a conduction velocity of ~>10 m/s) are denoted by the red circles. The Ad fibers (having a conduction velocity of ~10-3 m/s) are denoted by the blue squares. A pulse width (plateau phase) dependent suppression of compound action potential propagation can be observed in the proximal direction (solid symbols) for both A and Ad fiber types, with a preference for propagation distally (open symbols). Virtual cathode/anode formation occurs close to 1 mA. Quasitrapezoidal stimulation conveys a benefit (lower current requirements to achieve directionality) over square wave stimulation to achieve directionality. The pulse durations (0.1-0.6 msec) refer to the duration of the pulse where the peak amplitude is provided (i.e. the plateau of the quasitrapezoidal wave before the amplitude begins to decay).

Experimental Results (FIGS. 11A-D)

FIGS. 11A-D illustrate the results of tripolar quasitrapezoidal stimulation (0.1-0.6 msec plateau phase, >200 us decay) of guinea pig vagus using cuff design #1 where the cathode (electrode B) is 3× the geometric surface area of the anodes (electrode A and C). Positive output of a single stimulator is shorted to the outer two electrodes. A differential charge density on anodes is achieved through design spacings only, using a single current stimulator. The stimulation was provided with one current source attached to the central cathode and both anodes (i.e. 'passive control' was provided).

The A fibers (having a conduction velocity of ~>10 m/s) are denoted by the red circles. The Ad fibers (having a conduction velocity of ~10-3 m/s) are denoted by blue squares. A pulse width (plateau phase) dependent suppression of compound action potential propagation can be observed in both proximal (solid symbols) and distal (open symbols) directions for both A and Ad fiber types. Virtual cathode/anode formation no longer occurs in tripolar configuration. The C-fibers (denoted by green triangles) are shown for reference. This configuration allows a preference for high threshold fiber types with a suppression of lower threshold fiber types in both directions.

Experimental Results (FIGS. 12A-D)

FIGS. 12A-D illustrate the results of tripolar quasitrapezoidal stimulation (0.1-0.6 msec plateau phase, >200 us decay) of guinea pig vagus using cuff design #2 where cathode (electrode B) is 2× the geometric surface area of the anodes (electrode A and C). Positive output of a single stimulator is shorted to the outer two electrodes. A differential charge density on the anodes is achieved through design spacings only, using a single current stimulator). The stimulation was provided with one current source attached to the central cathode and both anodes (i.e. 'passive control' was provided).

The A fibers (having a conduction velocity of ~>10 m/s) are denoted by the red circles. The Ad fibers (having a conduction velocity of ~10-3 m/s) are denoted by the blue squares. A pulse width (plateau phase) dependent suppression of compound action potential propagation can be observed in the proximal direction (solid symbols) for both A and Ad fiber types, with a preference for propagation distally (open symbols). Virtual cathode/anode formation occurs close to 1 mA.

Figure 15V:
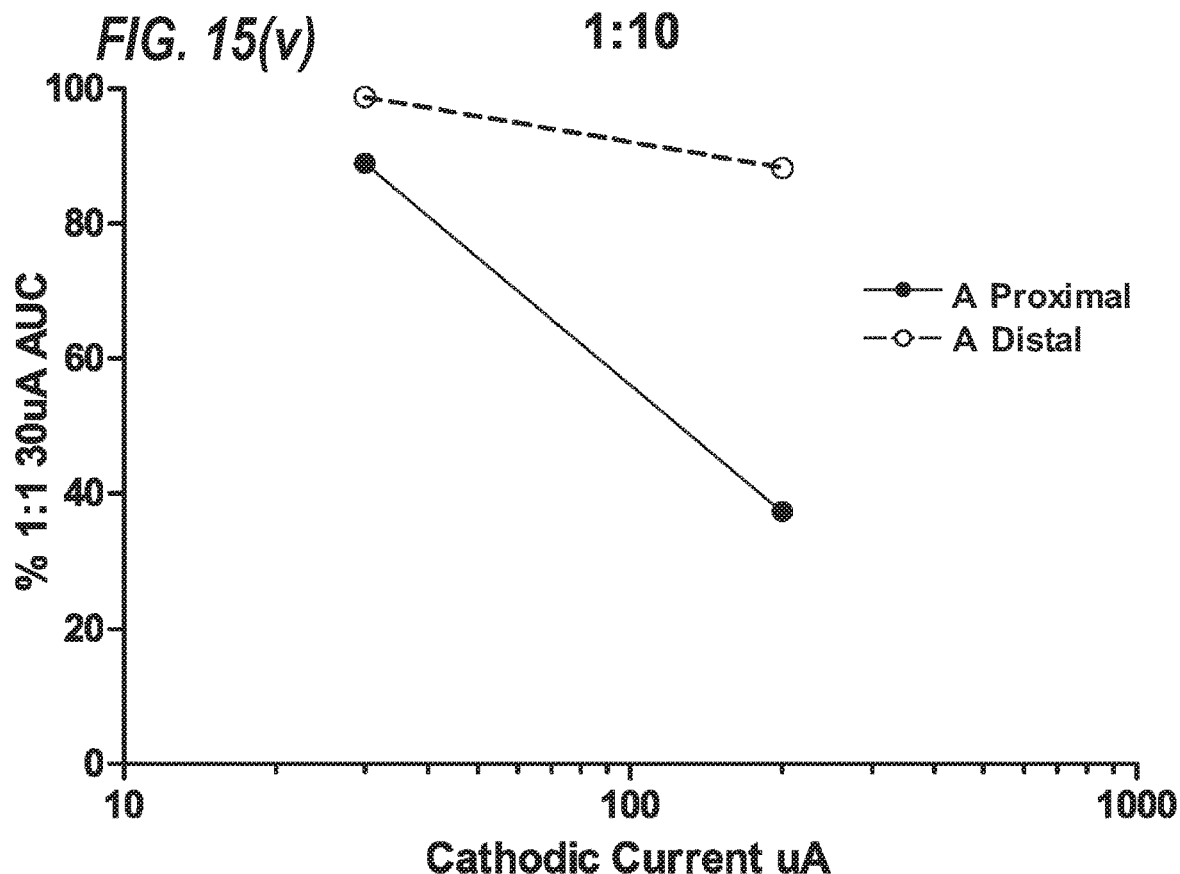
FIG. 15 illustrates action potential propagation when the electrode configuration of FIG. 7 is stimulated in a tripolar manner with a quasitrapezoidal pulse utilizing two current sources.
Figure 15:
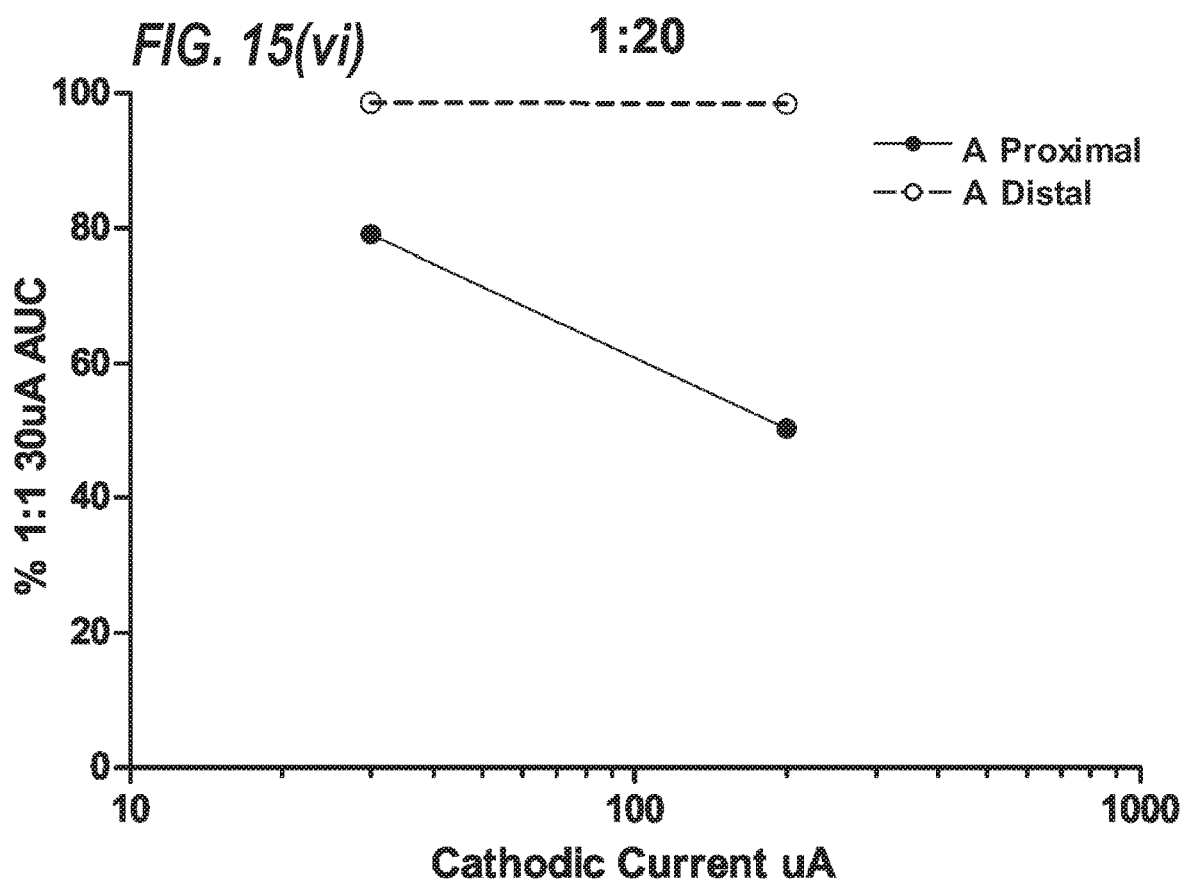

Experimental Results (FIG. 15)

The charts illustrated in FIG. 15 show the results of using tripolar quasitrapezoidal stimulation (0.4 msec plateau phase, >200 us decay) of a guinea pig vagus using cuff design #1 with a dual current stimulator configuration. In this example, two current sources are utilized to differentially control the arresting anode charge density (i.e. 'active control' was applied). The plateau width and decay time constants for both waveforms were matched and only amplitude varied. The reported cathodic amplitude is the sum of both stimulator amplitudes.

The amplitude ratios between the escape and arrest anode varied from 1:1 (50% of total current on arresting electrode) to 1:20 (95% of total current on the arresting anode) and 0:1 (bipolar, 100% of current on arresting anode) served as a comparator. The effect of varying the escape (distal facing) to arresting (proximal facing) anode current ratios are shown for A fibers having a conduction velocity of ~>10 m/s (red circles).

The percentage of maximal AUC for proximal propagation (solid circles compared to the percentage of maximal AUC for distal propagation (open circles) are shown for varying escape/arrest anode current ratios . . . . A preference for distal compared to proximal Ecap propagation (as illustrated by the blue squares) at 200 uA is shown for all configurations. A preference for directionality was maximized with 85% of current on the arresting anode (1:6.7).

Figure 13:
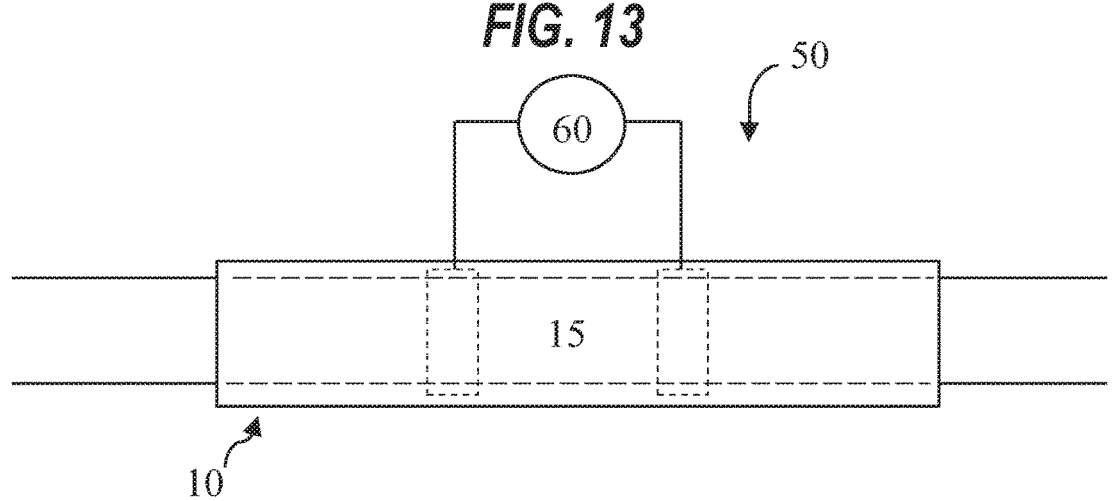
FIG. 13 illustrates a neural stimulation system.

Neural Stimulation System (FIG. 13)

The neural interface device 10 may be part of a neural stimulation system 50, as shown in FIG. 13. The neural stimulation system comprises a voltage or current source 60 which is electrically connected to the electrodes of the electrode arrangement 15 of the neural interface device 10, wherein the voltage or current source is configured to generate an electrical signal to be applied to the nerve via the electrode arrangement 15. The electrical signal causes unidirectional stimulation of neural activity in the nerve.

The electrical signal applied to the nerve is ideally non-destructive. As used herein, a "non-destructive signal" is a signal that, when applied, does not irreversibly damage the underlying neural signal conduction ability of the nerve. That is, application of a non-destructive signal maintains the ability of the nerve or fibers thereof, or other nerve tissue to which the signal is applied, to conduct action potentials when application of the signal ceases, even if that conduction is in practice artificially stimulated as a result of application of the non-destructive signal.

Stimulation of the neural activity of the nerve can be achieved using electrical signals which serve to replicate the normal neural activity of the nerve (i.e. the action potentials). Accordingly, the electrical signal may be a pulse train, the pulse train comprising a plurality of pulses. The number of pulses per second in the pulse train is set by the frequency, and the duration of the pulses within each phase is determined by the pulse width.

According to the disclosure, compound action potentials are impeded by adapting the pulse width of the electrical signal applied to the nerve based on the width of the gap between the electrodes in the previously described bipolar electrode arrangement of neural interface device 10 (i.e. the width of first gap $g_1$).

In particular, the pulse width must be set above a lower limit. The lower limit for the pulse width is the width of the first gap $g_1$ plus the width of the second electrode 12, then divided by the slowest conduction velocity of the fiber types of interest. The pulse width may be any value above the lower limit.

The pulses may have a sawtooth, sinusoidal, triangular, trapezoidal, square, or quasitrapezodial waveform, though a quasitrapezodial waveform can be advantageous. Other complex waveforms which are similar to the waveform of an action potential are also suitable with the disclosure.

The pulses may be biphasic pulses. The term "biphasic" refers to an electrical signal which causes each of the electrodes in the electrode arrangement 15 to be both positively and negatively charged over time. Biphasic pulses may be charge-balanced. The term "charge-balanced" in relation to a pulse train is taken to mean that the positive charge and negative charge applied by the signal over the pulse duration is equal.

Each pulse may have a duration of between 0.05 ms and 1.0 ms, and the current of the signal provided may be 300 μA. In particular, the pulses may have a duration of at least one of: 0.1 ms, 0.2 ms, 0.4 ms and 0.6 ms.

In addition to the neural interface device 10 and voltage or current source 60, the neural stimulation system 50 may comprise one or more of the following components: a microprocessor 113; an implantable transceiver 110; a physiological sensor 111; a power source 112; a memory 114 (otherwise referred to as a non-transitory computer-readable storage device); and a physiological data processing module 115.

Figure 14:
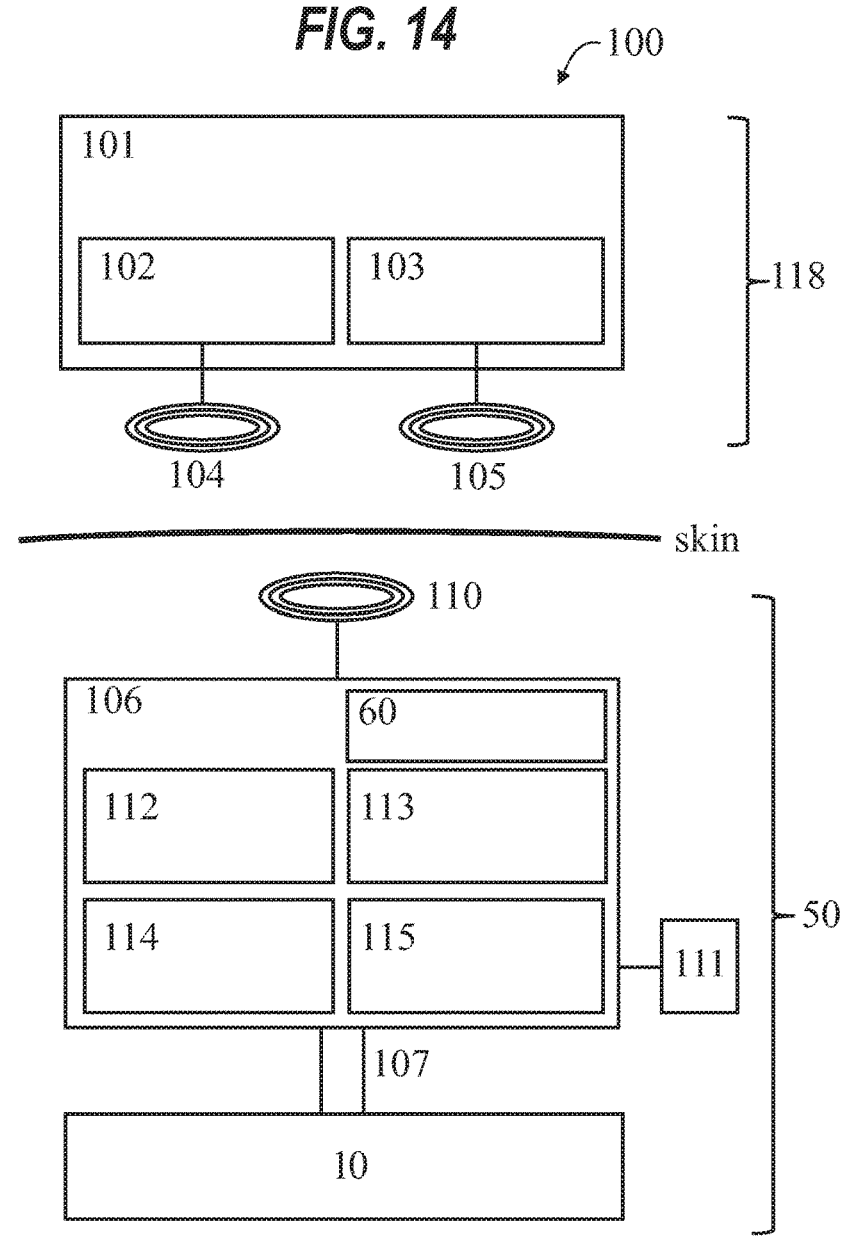
FIG. 14 illustrates a wider system including the neural stimulation system.

As shown in FIG. 14, one or more of the following components may be contained within an implantable device 106: the voltage or current source 60, the power source 112; the memory 114; the microprocessor 113, and the physiological data processing module 115.

The microprocessor 113 may be responsible for triggering the beginning and/or end of the electrical signals to be applied to the nerve. Optionally, microprocessor 113 may also be responsible for generating and/or controlling the signal parameters, including the pulse width.

The microprocessor 113 may be configured to operate in an open-loop fashion, wherein a pre-defined signal (e.g. as described above) is applied to the nerve at a given periodicity (or continuously) and for a given duration (or indefinitely) with or without an external trigger, and without any control or feedback mechanism. Alternatively, the microprocessor 113 may be configured to operate in a closed-loop fashion, wherein an electrical signal is applied based on a control or feedback mechanism. As described elsewhere herein, the external trigger may be an external controller 101 operable by the operator to initiate application of an electrical signal.

The microprocessor 113 may be constructed so as to generate, in use, a preconfigured and/or operator-selectable signal that is independent of any input. Alternatively, the microprocessor 113 may be responsive to an external signal, for example information (e.g. data) pertaining to one or more physiological parameters of the subject in which the neural stimulation system 50 is implanted.

The microprocessor 113 may be triggered upon receipt of a signal generated by an operator, such as a physician or the subject in which the neural stimulation system 50 is implanted. To that end, the neural stimulation system 50 may be part of a wider system 100 which additionally comprises an external system 118 comprising a controller 101. An example of the wider system 100 is described below.

External system 118 of wider system 100 is external the neural stimulation system 50 and external to the subject, and comprises controller 101. Controller 101 may be used for controlling and/or externally powering neural stimulation system 50. To this end, controller 101 may comprise a powering unit 102 and/or a programming unit 103. The external system 118 may further comprise a power transmission antenna 104 and a data transmission antenna 105, as further described below.

The controller 101 and/or microprocessor 113 may be configured to apply the electrical signal to the nerve periodically or continuously. Periodic application of an electrical signal involves applying the signal in an (on-off)$_n$ pattern, where n>1. For instance, the electrical signal can be applied continuously for a duration of time, before ceasing for a period, before being again applied continuously for a second duration of time, etc.

The signal may be applied by controller 101 and/or microprocessor 113 for a specific amount of times per day. For instance, the signal may be applied in bursts across the day.

Continuous application may continue indefinitely, e.g. permanently. Alternatively, the continuous application may be for a minimum period, for example the signal may be continuously applied for at least 5 days, or at least 7 days.

Whether the signal applied to the nerve is controlled by controller 101, or whether the signal is continuously applied directly by microprocessor 113, although the signal might be a series of pulses, the gaps between those pulses do not mean the signal is not continuously applied.

The signal may be applied only when the subject is in a specific state e.g. only when the subject is awake, only when the subject is asleep, prior to and/or after the ingestion of food, prior to and/or after the subject undertakes exercise, etc.

Timing for stimulation of neural activity in the nerve may be achieved using controller 101.

The power source 112 may comprise a current source and/or a voltage source for providing power to the current or voltage source 50. The power source 112 may also provide power for the other components of the implantable device 106 and/or neural stimulation system 50, such as the microprocessor 113, memory 114, and implantable transceiver 110. The power source 112 may comprise a battery, the battery may be rechargeable.

It will be appreciated that the availability of power is limited in implantable devices, and embodiments of the disclosure have been devised with this constraint in mind.

The implantable device 106 and/or neural stimulation system 50 may be powered by inductive powering or a rechargeable power source.

Memory 114 may store power data and data pertaining to the one or more physiological parameters from internal neural stimulation system 50. For instance, memory 114 may store data pertaining to one or more signals indicative of the one or more physiological parameters detected by physiological sensor 111, and/or the one or more corresponding physiological parameters determined via physiological data processing module 115. In addition or alternatively, memory 114 may store power data and data pertaining to the one or more physiological parameters from external system 118 via the implantable transceiver 110. To this end, the implantable transceiver 110 may form part of a communication subsystem of the wider system 100, as is further discussed below.

The physiological data processing module 115 is configured to process one or more signals indicative of one or more physiological parameters in a subject detected by the physiological sensor 111, to determine one or more corresponding physiological parameters. Physiological data processing module 115 may be configured for reducing the size of the data pertaining to the one or more physiological parameters for storing in memory 114 and/or for transmitting to the external system via implantable transceiver 110. Implantable transceiver 110 may comprise an one or more antenna(e). The implantable transceiver 100 may use any suitable signaling process such as RF, wireless, infrared and so on, for transmitting signals outside of the body, for instance to wider system 100 of which the neural stimulation system 50 is one part.

Alternatively or additionally, physiological data processing module 115 may be configured to process the signals indicative of the one or more physiological parameters and/or process the determined one or more physiological parameters to determine the evolution of the disease in the subject. In such case, the neural stimulation system 50, in particular the implantable device 106, will include a capability of calibrating and tuning the signal parameters based on the one or more physiological parameters of the subject and the determined evolution of the disease in the subject.

The physiological data processing module 115 and the at least one physiological sensor 111 may form a physiological sensor subsystem, also known herein as a detector, either as part of the neural stimulation system 50, part of the implantable device 106, or external to the system.

Physiological sensor 111 comprises one or more sensors, each configured to detect a signal indicative of one of the one or more physiological parameters described above. For example, the physiological sensor 110 is configured for: detecting biomolecule concentration using electrical, RF or optical (visible, infrared) biochemical sensors; detecting blood flow using intra- or perivascular flow tubes in or around an artery; detecting neural activity of a nerve using an electrical sensor; or a combination thereof.

The physiological parameters determined by the physiological data processing module 115 may be used to trigger the microprocessor 113 to apply an electrical signal to the nerve via the electrode arrangement 15. Upon receipt of the signal indicative of a physiological parameter received from physiological sensor 111, the physiological data processor 115 may determine the physiological parameter of the subject, and the evolution of the disease, by calculating in accordance with techniques known in the art.

The memory 114 may store physiological data pertaining to normal levels of the one or more physiological parameters. The data may be specific to the subject into which the neural stimulation system 50 is implanted, and gleaned from various tests known in the art. Upon receipt of the signal indicative of a physiological parameter received from physiological sensor 111, or else periodically or upon demand from physiological sensor 111, the physiological data processor 115 may compare the physiological parameter determined from the signal received from physiological sensor 111 with the data pertaining to a normal level of the physiological parameter stored in the memory 114, and determine whether the received signals are indicative of insufficient or excessive of a particular physiological parameter, and thus indicative of the evolution of the disease in the subject.

The neural stimulation system 50 may be configured such that if and when an insufficient or excessive level of a physiological parameter is determined by physiological data processor 115, the physiological data processor 115 triggers application of the electrical signal to the nerve via the electrode arrangement 15, in the manner described elsewhere herein. For instance, if physiological parameter indicative of worsening of any of the physiological parameters and/or of the disease is determined, the physiological data processor 115 may trigger application of an electrical signal which dampens secretion of the respective biochemical, as described elsewhere herein. Particular physiological parameters relevant to the present disclosure are described above.

When one or more signals indicative of one or more of these physiological parameters are received by the physiological data processor 115, an electrical signal may be applied to the nerve via the electrode arrangement 15.

Controller 101 may be configured to make adjustments to the operation of the neural stimulation system 50. The data may be specific to the patient into which the device is implanted. The controller 101 may also be configured to make adjustments to the operation of the power source 112, signal generator 60 and processing elements 113, 115 and/or neural interfacing element 10 in order to tune the electrical signal applied to the nerve via the electrode arrangement 15.

Wider System (FIG. 14)

With reference to FIG. 14, the neural stimulation device may be part of a wider system 100 that includes a number of subsystems, for example the external system 118. The external system 118 may be used for powering and programming the neural stimulation system 50 through human skin and underlying tissues.

The external subsystem 118 may comprise, in addition to controller 101, one or more of: a powering unit 102, for wirelessly recharging the battery of power source 112 used to power the implantable device 106; and a programming unit 103 configured to communicate with the implantable transceiver 110. The programming unit 103 and the implantable transceiver 110 may form a communication subsystem. The powering unit 102 may be housed together with programing unit 103; alternatively, they can be housed in separate devices.

The external subsystem 118 may also comprise one or more of: power transmission antenna 104; and data transmission antenna 105. Power transmission antenna 104 may be configured for transmitting an electromagnetic field at a low frequency (e.g., from 30 kHz to 10 MHz). Data transmission antenna 105 may be configured to transmit data for programming or reprogramming the implantable device 106, and may be used in addition to the power transmission antenna 104 for transmitting an electromagnetic field at a high frequency (e.g., from 1 MHz to 10 GHz). The temperature in the skin will not increase by more than 2 degrees Celsius above the surrounding tissue during the operation of the power transmission antenna 104. The at least one antennae of the implantable transceiver 110 may be configured to receive power from the external electromagnetic field generated by power transmission antenna 104, which may be used to charge the rechargeable battery of power source 112.

The power transmission antenna 104, data transmission antenna 105, and the at least one antennae of implantable transceiver 110 have certain characteristics such a resonant frequency and a quality factor (Q). One implementation of the antenna(e) is a coil of wire with or without a ferrite core forming an inductor with a defined inductance. This inductor may be coupled with a resonating capacitor and a resistive loss to form the resonant circuit. The frequency is set to match that of the electromagnetic field generated by the power transmission antenna 105. A second antenna of the at least one antennae of implantable transceiver 110 can be used in neural stimulation system 50 for data reception and transmission from/to the external system 118. If more than one antenna is used in the neural stimulation system 50, these antennae are rotated 30 degrees from one another to achieve a better degree of power transfer efficiency during slight misalignment with the with power transmission antenna 104.

External system 118 may comprise one or more external body-worn physiological sensors 121 (not shown) to detect signals indicative of one or more physiological parameters. The signals may be transmitted to the neural stimulation system 50 via the at least one antennae of implantable transceiver 110. Alternatively or additionally, the signals may be transmitted to the external neural stimulation system 50 and then to the neural stimulation system 50 via the at least one antennae of implantable transceiver 110. As with signals indicative of one or more physiological parameters detected by the implanted physiological sensor 111, the signals indicative of one or more physiological parameters detected by the external sensor 121 may be processed by the physiological data processing module 115 to determine the one or more physiological parameters and/or stored in memory 114 to operate the neural stimulation system 50 in a closed-loop fashion. The physiological parameters of the subject determined via signals received from the external sensor 121 may be used in addition to alternatively to the physiological parameters determined via signals received from the implanted physiological sensor 111.

The wider system 100 may include a safety protection feature that discontinues the electrical stimulation of the nerve in the following exemplary events: abnormal operation of the neural stimulation system 50 (e.g. overvoltage); abnormal readout from an implanted physiological sensor 111 (e.g. temperature increase of more than 2 degrees Celsius or excessively high or low electrical impedance at the electrode-tissue interface); abnormal readout from an external body-worn physiological sensor 121 (not shown); or abnormal response to stimulation detected by an operator (e.g. a physician or the subject). The safety precaution feature may be implemented via controller 101 and communicated to the neural stimulation system 50, or internally within the neural stimulation system 50.

The external system 118 may comprise an actuator 120 (not shown) which, upon being pressed by an operator (e.g. a physician or the subject), will apply the electrical signal, via controller 101 and the respective communication subsystem, to trigger the microprocessor 113 of the neural stimulation system 50 to apply the electrical signal to the nerve by the electrode arrangement 15.

Wider system 100 of the disclosure, in particular neural stimulation system 50, can be made from, or coated with, a biostable and biocompatible material. This means that the system is both protected from damage due to exposure to the body's tissues and also minimizes the risk that the system elicits an unfavorable reaction by the host (which could ultimately lead to rejection). The material used to make or coat the system should ideally resist the formation of biofilms. Suitable materials include, but are not limited to, poly(p-xylylene) polymers (known as Parylenes) and polytetrafluoroethylene.

General

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards etc. and do not include propagated signals. The software can be suitable for execution on a parallel processor or a serial processor such that the method steps may be carried out in any suitable order, or simultaneously. This acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Unless otherwise indicated each embodiment as described herein may be combined with another embodiment as described herein. The term "comprising" encompasses "including" as well as "consisting" e.g. a composition "comprising" X may consist exclusively of X or may include something additional e.g. X+Y.

It will be understood that the benefits and advantages described above may relate to one embodiment or may relate to several embodiments. The embodiments are not limited to those that solve any or all of the stated problems or those that have any or all of the stated benefits and advantages.

It will be understood that the above description of embodiments is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention.

The invention claimed is:

1. A neural interface device for unidirectional stimulation of a target comprising at least one A-type nerve fiber or at least one at least partially myelinated nerve fiber, the neural interface device comprising:
an electrode arrangement configured to be placed on or around the target and in contact with the target, the electrode arrangement comprising:
a first anodal electrode having a first surface area, and configured to be positively charged, and
a second cathodal electrode having a second surface area configured to be negatively charged and spaced apart from the first anodal electrode so as to define a first gap along a longitudinal axis of the target;
wherein the second surface area is larger than the first surface area and wherein the first anodal electrode and the second cathodal electrode are paired such that a first charge concentration on the first anodal electrode exceeds a second charge concentration on the second cathodal electrode for any given current injection; and
further comprising a mount upon which the electrode arrangement is mounted, the mount comprising a first non-conductive portion and a second non-conductive portion,
wherein the first non-conductive portion is positioned between and extends contiguously between the first anodal electrode and a first end of the mount, and the second non-conductive portion is positioned between and extends contiguously between the second cathodal electrode and a second end of the mount.

2. The neural interface device of claim 1, wherein the first anodal electrode has a first width and the second cathodal electrode has a second width, and the second width is larger than the first width, and further wherein the first width and the second width extend in a direction of the longitudinal axis of the target when the neural interface device is placed around the target.

3. The neural interface device of claim 2, wherein the second width is less than or equal to five times the first width.

4. The neural interface device of claim 1, wherein the second surface area is three times the first surface area.

5. The neural interface device of claim 1, wherein at least one of:
a surface area of the second non-conductive portion is larger than a surface area of the first non-conductive portion,
a width of the second non-conductive portion is larger than a width of the first non-conductive portion,
the surface area of the second non-conductive portion is at least or greater than twice as large as the surface area of the second cathodal electrode, or
the surface area of the second non-conductive portion is at least or greater than twice as large as the surface area of the second cathodal electrode.

6. The neural interface device of claim 1, further comprising a flexible non-conductive layer, wherein the electrode arrangement is mounted on the flexible nonconductive layer, and wherein at least one of:
the flexible non-conductive layer is configured to at least partially circumvent the target;
wherein when the neural interface device is placed around the target the flexible non-conductive layer is configured to form a cuff around the target, the cuff having a first open end and a second open end spaced apart along the longitudinal axis of the target;
the electrode arrangement is spaced apart from the first open end by a second gap and is spaced apart from the second open end by a third gap;
the second gap has a width, in the direction of the longitudinal axis of the target when the neural interface device is placed around the target, which is approximately equal to three times the width of the first gap; or
the third gap has a width, in the direction of the longitudinal axis of the target when the neural interface device is placed around the nerve, which is larger than two times a width of the first electrode.

7. A system for unidirectional stimulation of a target comprising at least one A-type nerve fiber or at least one at least partially myelinated nerve fiber, the system comprising:
one or more neural interface devices of claim 6; and
a voltage source or a current source electrically connected to the electrode arrangement, wherein the voltage source or the current source is configured to generate an electrical signal to be applied to the target via the electrode arrangement.

8. The system of claim 7, wherein the voltage source or the current source is configured to apply the electrical signal to the electrode arrangement such that the first anodal electrode becomes positively charged and the second cathodal electrode becomes negatively charged.

9. The system of claim 8, further comprising an additional voltage source or an additional current source electrically connected to the electrode arrangement, wherein the additional voltage source or the additional current source is configured to generate an electrical signal to be applied to the nerve via the electrode arrangement; and wherein the additional voltage source or the additional current source is configured to apply the electrical signal to the electrode arrangement such that the third electrode becomes positively charged and the second cathodal electrode becomes negatively charged.

10. The system of claim 7, wherein the electrical signal comprises a pulse train, the pulse train comprising a plurality of pulses.

11. The system of claim 10, wherein, in use, at least one of:
the pulses have a pulse width which is less than or equal to the width of the first anodal electrode divided by a conduction velocity of action potentials in the nerve fiber around which the neural interface device is placed;
the pulses have a pulse width which is less than or equal to the sum of the width of the second cathodal electrode and the second gap divided by the conduction velocity of action potentials in the
nerve fiber around which the neural interface device is placed;
the pulses have a pulse width which is greater than or equal to the width of the first gap divided by the conduction velocity of action potentials in the nerve fiber around which the neural interface device is placed;
the pulses have a pulse width of at least the sum of the width of the first anodal electrode and width of the second cathodal electrode, divided by the conduction velocity of action potentials in the nerve fiber around which the neural interface device is placed; or
the pulses have a pulse width of at least the sum of the width of the first gap and the width of the second electrode, divided by the conduction velocity of action potentials in the nerve fiber around which the neural interface device is placed.

12. The system of claim 7, wherein the voltage source or the current source is configured to apply the electrical signal to the electrode arrangement such that the first anodal electrode and the third electrode become positively charged and the second cathodal electrode becomes negatively charged.

13. The system of claim 12, wherein the electrical signal comprises a pulse train, the pulse train comprising a plurality of pulses.

14. The neural interface device of claim 1, further comprising:
a third electrode having a third surface area, and configured to be positively charged and spaced apart from the second cathodal electrode so as to define a second gap along the longitudinal axis of the target;
wherein the electrode arrangement is arranged in an asymmetric configuration.

15. The neural interface device of claim 14, wherein the asymmetric configuration comprises the first anodal electrode being configured to be positively charged with a first current and the third electrode being configured to be positively charged with a second current different from the first current.

16. The neural interface device of claim 14, wherein the first gap is different from the second gap.

17. The neural interface device of claim 14, wherein the first electrode is arranged to provide a different charge to the third electrode.

18. The neural interface device of claim 14, wherein the asymmetric configuration comprises the first anodal electrode and the third electrode being configured to be positively charged with different currents; and wherein the first electrode, the second cathodal electrode, and the third electrode have the same surface area.

19. A computer system comprising:
at least one processor and memory storing a computer program comprising code portions which, when loaded and run on a computing device, cause the computing device to:
generate an electrical signal to be applied to a target comprising at least one A-type nerve or at least one at least partially myelinated nerve fiber via the electrode arrangement of the neural interface device of claim 14 and least one voltage source or at least one current source electrically connected to the electrode arrangement.

20. The computer system of claim 19, wherein the nerve fibers are selectively stimulated with a higher activation threshold by creating a bidirectional block of A-fibers.

21. A non-transitory computer-readable medium storing a computer program comprising code portions which, when loaded and run on a computing device, cause the computing device to generate an electrical signal to be applied to a target comprising at least one A-type nerve or at least one at least partially myelinated nerve fiber via the electrode arrangement of the neural interface device of claim 14 and least one voltage source or at least one current source electrically connected to the electrode arrangement.

22. The non-transitory computer-readable medium of claim 21, wherein the nerve fibers are selectively stimulated with a higher activation threshold by creating a bidirectional block of A-fibers.

* * * * *